United States Patent
Runeman et al.

(10) Patent No.: US 7,482,023 B2
(45) Date of Patent: Jan. 27, 2009

(54) HYGIENE TISSUE WITH LACTIC ACID PRODUCING BACTERIAL STRAINS

(75) Inventors: Bo Runeman, Partille (SE); Ulla Forsgren-Brusk, Pixbo (SE); Ingemar Fernfors, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 204 days.

(21) Appl. No.: 10/689,762

(22) Filed: Oct. 22, 2003

(65) Prior Publication Data

US 2004/0142832 A1 Jul. 22, 2004

Related U.S. Application Data

(60) Provisional application No. 60/437,742, filed on Jan. 3, 2003.

(51) Int. Cl.
*A61K 7/00* (2006.01)
(52) U.S. Cl. ........................ 424/484; 510/130
(58) Field of Classification Search ........................ None
See application file for complete search history.

(56) References Cited

U.S. PATENT DOCUMENTS

| | | | | |
|---|---|---|---|---|
| 5,763,332 | A * | 6/1998 | Gordon et al. | 442/84 |
| 2003/0143262 | A1 * | 7/2003 | Brusk et al. | 424/443 |
| 2003/0224034 | A1 * | 12/2003 | Koenig | 424/443 |

FOREIGN PATENT DOCUMENTS

| EP | 1 118 342 | 7/2001 |
|---|---|---|
| SE | 518097 | 8/2002 |
| WO | 92/13577 | 8/1992 |
| WO | 97/02846 | 1/1997 |
| WO | 99/17813 | 4/1999 |
| WO | 99/45099 | 9/1999 |
| WO | 00/35502 | 6/2000 |
| WO | 01/13956 A2 | 3/2001 |
| WO | 01/13956 A3 | 3/2001 |
| WO | 02/28446 | 4/2002 |

OTHER PUBLICATIONS

Hill, G.B., et al., "Bacteriology of the Vagina", Scand. J. Urol. Nephrol. 1984; 86 (suppl.) 23-39.

Runeman, B., et al., "Experimental *Candida albicans* Lesions in Healthy Humans: Dependence on Skin pH", Acta Derm Venereol 2000; 80: 421-424, Taylor & Francis.

Arkadeva, A., et al., N.A. Nauchnye Doklady Vysshei Shkoly. , Biologicheskie Nauki 1983, 2:101-104.

(Continued)

*Primary Examiner*—Necholus Ogden, Jr.
(74) *Attorney, Agent, or Firm*—Buchanan Ingersoll & Rooney

(57) ABSTRACT

A hygiene tissue is used for both cleaning and transferring lactic acid producing bacteria to the skin and urogenital area. The hygiene tissue contains, on separate parts of the tissue, cleaning liquid and a bacterial composition. Bacterial viability and transfer ability is maintained by suspending the bacteria in a lipid which protects the bacteria from moisture. The lipid also enhances transfer of the bacteria from the tissue to the skin or urogenital area. Different designs of the hygiene tissue prevent the mixing of the cleaning liquid and the bacterial composition.

37 Claims, 13 Drawing Sheets

OTHER PUBLICATIONS

Stoianova et al., Mikroliologiia, 2000, 69:98-104.

*Harry's Cosmeticology*, 8th ed., Ed. by M.M. Rieger, Chemical Publishing Co., Inc., New York 2000, p. 116-121, p. 308-315, p. 323-331, p. 359-363, p. 380-381.

Prior, B.A., "Measurement of Water Activity in Foods: A Review", Journal of Food Protection, vol. 42, No. 8, pp. 668-674 (Aug. 1979) Int. Assoc. of Milt, Food & Environmental Sanitarians.

"Fundamentals of Water Activity", Apr. 28, 1999, available at www.decagon.com/aqualab/.

* cited by examiner

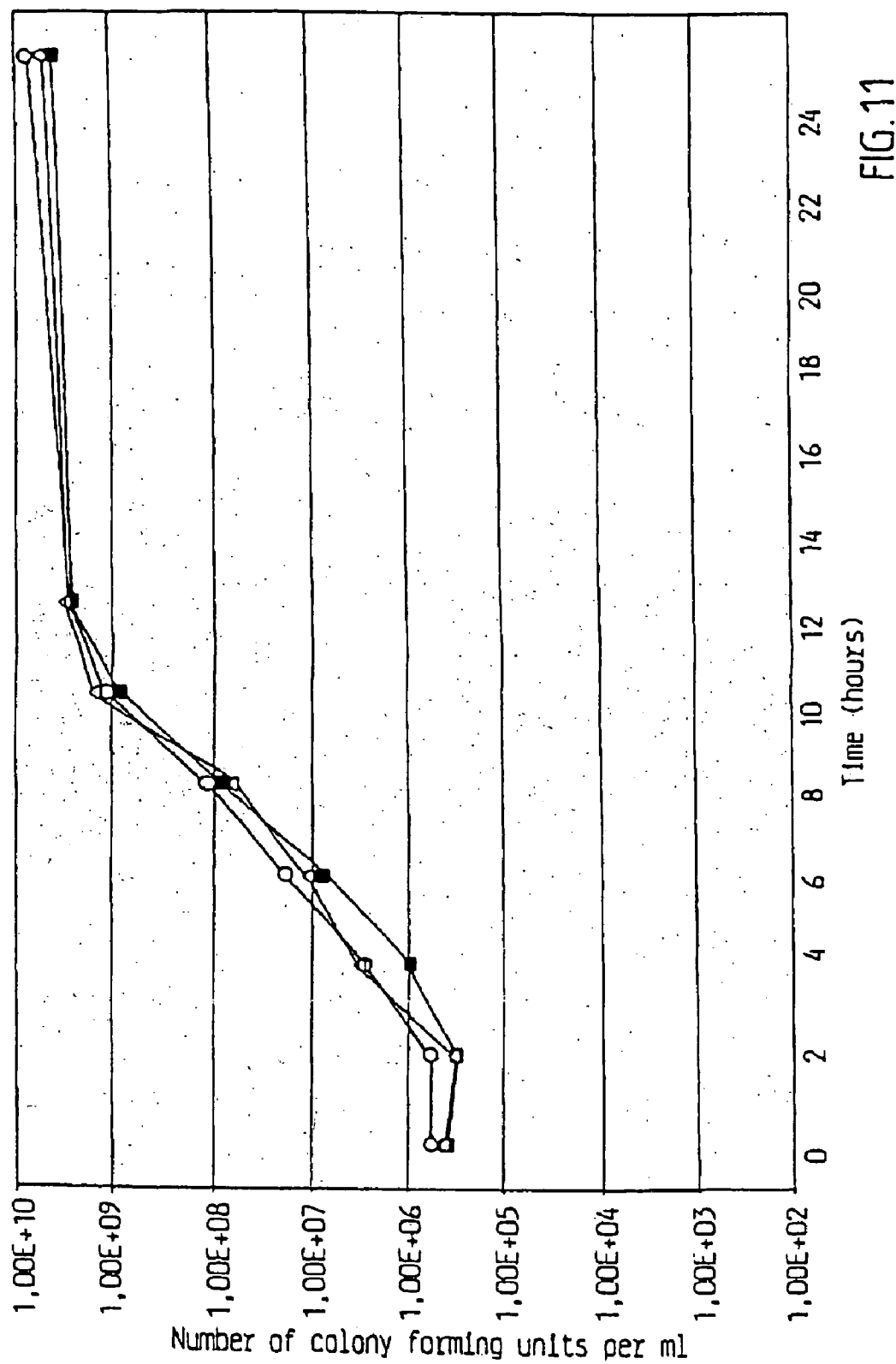

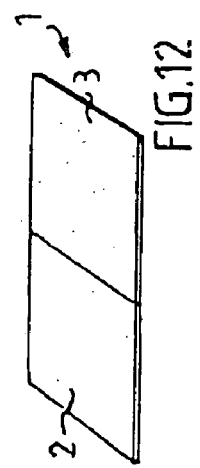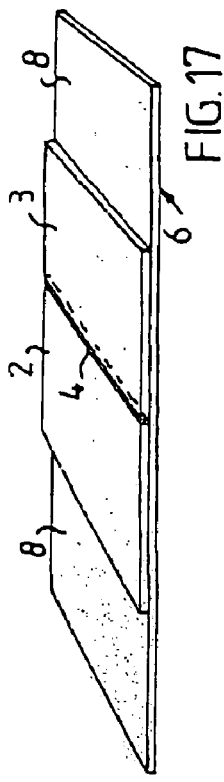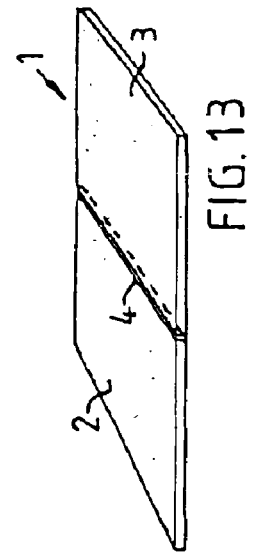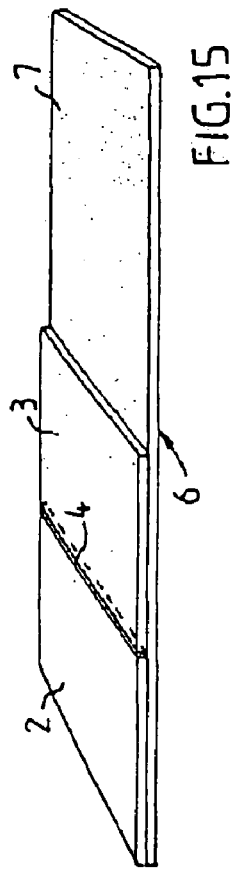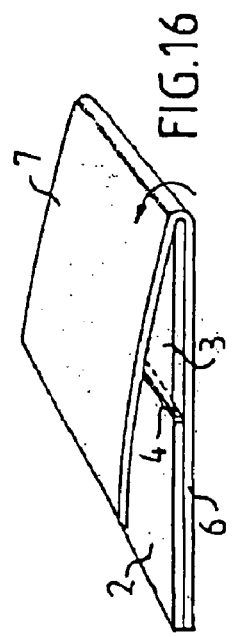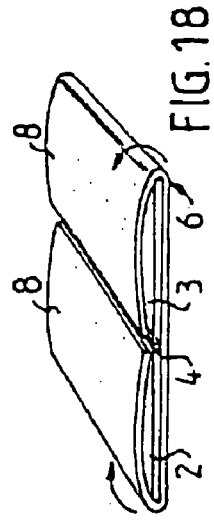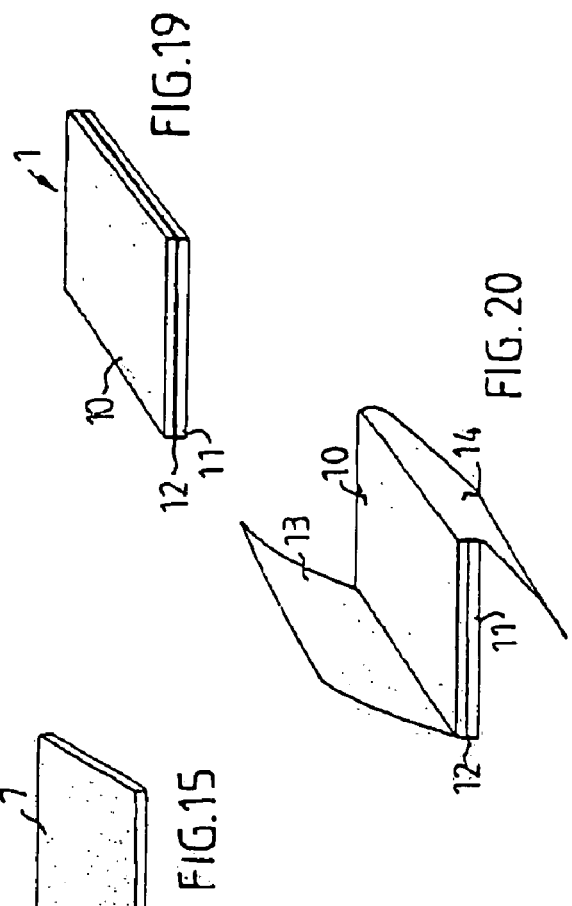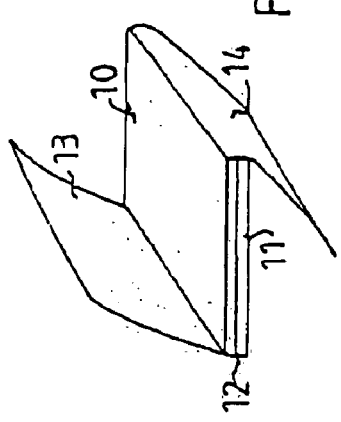

HYGIENE TISSUE WITH LACTIC ACID PRODUCING BACTERIAL STRAINS

CROSS-REFERENCE TO RELATED APPLICATIONS

The present application claims the benefit of U.S. Provisional Application No. 60/437,742, filed in the United States on Jan. 3, 2003, the entire contents of which are hereby incorporated herein by reference.

FIELD OF THE INVENTION

The present invention relates to hygiene tissue to be used for cleaning of and transfer of lactic acid producing bacteria to the skin and urogenital area.

BACKGROUND OF THE INVENTION

The urogenital area harbors a complex microbial ecosystem comprising more than 50 different bacterial species (Hill et al., Scand. J. Urol. Nephrol. 1984;86 (suppl.) 23-29). The dominating species in this area are lactic acid producing bacteria belonging to the genus *Lactobacillus*. These lactic acid producing members are important for retaining a healthy microbial flora in these areas, and act as probiotic bacteria with an antagonistic effect against pathogenic microbial species. Lactic acid producing bacteria inhibit growth and colonization by other microorganisms by occupying suitable niches for colonization, by forming biofilms and competing for available nutrients, thereby excluding colonization by harmful microorganisms. Also, the production of enzymes, such as hydrogen peroxidase, and specific inhibiting substances, such as toxins and bacteriocines, and organic acids (including lactic acid and acetic acid) that lower the pH, inhibit colonization by other microorganisms. However, the microbial ecosystem of a healthy individual can be disturbed by the use of antibiotics, in people suffering from diabetes and hormonal changes, such as during pregnancy, use of contraceptives with estrogen, during menstruation, after menopause, etc. Also, microorganisms can spread from the anus to the urogenital area, thereby causing infections. This results in a disturbance of the normal microbial flora and leaves the individual susceptible to microbial infections that cause vaginitis, urinary tract infections and ordinary skin infections. Microorganisms commonly associated with these kind of infections belong to the genera *Escherichia, Enterococcus, Psedomonas, Proteus, Klebsiella, Streptococcus, Staphylococcus, Gardnerella* and *Candida*. Women are at particular risk due to their shorter distance between the anus and the urogenital tract; especially at risk are young women, who do not yet have well-developed microflora in the urogenital area, and older women, who no longer have a protective flora.

Similarly to the urogenital area, the skin is colonized by an array of organisms, which form the normal flora. The numbers and identity of the organisms vary between different skin sites. This, together with the skin's structural barrier, provides the host with an excellent defense against invading microbes. The number of bacteria on the skin vary from a few hundred per $cm^2$ on the arid surfaces of the forearm and back, to tens of thousands per $cm^2$ on the moist areas such as the axilla and groin. This normal flora plays an important role in preventing 'foreign' organisms from colonizing the skin, but it too needs to be kept in check, in order to avoid skin infections.

*Staphylococcus aureus* is the most common cause of minor skin infections, such as boils or abscesses, as well as more serious post-operative wound infection. Treatment involves drainage and this is usually sufficient for minor lesions, but antibiotics may be given in addition when the infection is severe and the patient has fever. Toxic shock syndrome is a systemic infection caused by *S. aureus* strains which produce toxic shock syndrome toxin. The disease came to prominence through its association with tampon use by healthy women, but it is not confined to women and can occur as a result of *S. aureus* infection at non-genital sites.

Other common skin infections are caused by *Streptococcus pyogenes* (group A *streptococci*). The organisms are acquired through contact with other people with infected skin lesions and may first colonize and multiply on normal skin prior to invasion through minor breaks of the epithelium and the development of lesions. Treatment with penicillin or erythromycin may be necessary to combat the infection.

*Propionibacterium acnes* are found on normal human skin. The organism is no longer believed to be the cause of acne, but have been assigned a role in inflammation of acne.

*Malassezia* (formerly *Pityrosporum*) are probably universal inhabitants of the head and thorax in adult humans. Species of this organism are known to be involved in the skin diseases seborrhoeic dermatitis and pityriasis versicolor and to play a part in the aetiology of severe dandruff. These yeasts may also play a part in exacerbation of atopic dermatitis.

So-called ringworm infections of the skin may be caused by dermatophyte fungi, e.g., *Tricophyton, Epidermophyton* and *Microsporum*.

The relative dryness of most areas of skin limits the growth of *Candida*, which therefore are found in low numbers on healthy skin. However, *Candida* rapidly colonizes damaged skin and intertriginous sites (apposed skin sites which are moist and become chafed). *Candida* also colonizes the oral and vaginal *mucosa* and overgrowth may result in disease in these sites (so called thrush). *C. albicans* is associated with diaper dermatitis. A study has shown that *C. albicans*-induced lesions are remarkably influenced by pH, i.e., a lower skin pH results in less lesions (B. Runeman, Acta Derm Venereol 2000; 80: 421-424).

One way to reduce the problems with the kind of infections described above is to have good personal hygiene. However, excessive use of cleaning agents not only decreases the amount of harmful microbes, but can harm the beneficial microbial flora, rendering the skin susceptible to pathogenic species that colonize and cause infections. Alternatively, administration of lactic acid producing bacteria to the urogenital area and the skin in order to outcompete pathogenic species and to facilitate reestablishment and maintenance of a beneficial microbial flora in these areas, has been found to be a successful means to treat and prevent microbial infections.

It has been suggested that lactic acid producing bacteria can be delivered via absorbent articles, such as diapers, sanitary napkins, panty liners and tampons, as described in, for example, in WO97/02846, WO99/17813, WO99/45099 and WO00/35502. However, absorbent articles may not always be an optimal administration route, since carrying of an absorbent article often is apprehended as uncomfortable, indiscrete and warm. This administration route can also be inconvenient as repeated administration of lactic acid producing bacteria is often necessary to retain the efficacy of the treatment or the preventative effect. Also, these products cannot be used for delivery of the bacteria to other regions of the body than the urogenital area. Therefore, for some applications it can be more convenient to administer lactic acid producing bacteria by other means than absorbent products. A second problem with the administration of lactic acid producing bacteria via absorbent articles relates to the manufacturing of such products, since all possible variants and sizes of the product have to be supplied with the bacteria. Therefore the administration via a product that could be used without individual adjustments could provide a manufacturing advantage over the absorbent products.

However, a major problem with providing articles intended to be used for transfer of lactic acid producing bacteria, is that the bacteria have to retain viability during transport and storage of the articles. Lactic acid producing bacteria rapidly lose viability under moist conditions, and it is therefore important that the products are not exposed to moisture. One way to partly overcome this problem has been to supply articles with freeze-dried lactic acid producing bacteria, thereby providing long shelf-life products containing viable lactic acid producing bacteria. However, the bacteria still have to be protected against moisture during the time between manufacturing and use.

Alternatively, research experiments have shown that storage in sterile vaseline oil results in a high level of viable lactobacilli cells after 8 months of storage, although survival of the bacterial cells is not discussed in the context of transferring bacteria to the skin (Arkadéva et al., N A. Nauchnye Doklady Vysshei Shkoly. *Biologicheskie Nauki*, 1983, 2:101-104). In contrast, Stoianova et al. (*Mikrobiologiia*, 2000, 69:98-104) found that immersion in mineral oil was not effective to preserve viability of lactic acid producing bacteria. There are additional examples of the combination lactic acid producing bacteria and a fatty composition, although these do not describe the effect of the fatty composition on the survival of the lactic acid producing bacteria. WO01/13956 describes the use of pharmaceutical compositions comprising Emu oil, antimicrobial agents and/or *Bacillus coagulans* to be used for antimicrobial treatments. However, the object of using compositions described in WO01/13956 is to treat microbial infections by adding components that kill undesirable microorganisms and the Emu oil is not added to enhance survival of bacteria included in the compositions. WO92/13577 relates to a tampon or sanitary napkin that is coated with a compound with adhesive properties and subsequently added bacteria that attach to the adhesive compound. However, WO92/13577 does not relate to hygiene tissues.

In conclusion, prior to the present invention, there was still a need to develop products for delivery of lactic acid producing bacteria to the skin and urogenital area that are convenient to use, result in efficient transfer of the bacteria to the area where they are applied and can be stored for long time periods without loss of viability of the bacterial cells.

OBJECTS AND SUMMARY

An object of the present invention is to provide a convenient device that both allows cleaning of the skin and urogenital area and delivery of probiotic lactic acid producing bacteria. The present invention therefore pertains to a hygiene tissue to be used for cleaning and caring of the skin and the urogenital area and that also can be used to deliver lactic acid producing bacteria to these areas. According to one embodiment of the inventor, the hygiene tissue is supplied with a composition comprising a preparation of lactic acid producing bacterium/bacteria, preferably suspended in a lipid, and optionally, additional components and a cleaning liquid optionally comprising cleaning additives, the composition comprising the bacteria and the cleaning liquid being supplied to different parts of the hygiene tissue. The present inventors surprisingly found that encapsulating the lactic acid bacterium in a lipid provided a moisture-free environment keeping the bacterium in a shape that resulted in enhanced longevity, high transfer rates to the skin, and retention of fitness for survival and growth on the skin. Therefore, by this approach, bacterial survival was enhanced during long term storage. Also, the hygiene tissue of the present invention improved the efficiency of transfer of the lactic acid producing bacterium to the skin and urogenital area. Furthermore, the invention relates to the design of the hygiene tissue in order to prevent mixing of the cleaning agent and the bacterial composition.

BRIEF DESCRIPTION OF THE FIGURES

FIG. 1 shows the survival of *Lactobacillus plantarum* 931 in olive oil on hygiene tissues Spun Lace Dupont (♦) and SCA Absbond (■).

FIG. 2 shows the survival of *Lactobacillus plantarum* 931 in suspensions of water and olive oil on hygiene tissues (Spun Lace Dupont) with (♦) 10% olive oil in water and (■) 30% olive oil in water.

FIG. 3 shows the survival of *Lactobacillus plantarum* 931 in olive (♦) and rapeseed (■) oil.

FIG. 4 shows the survival of *Lactobacillus plantarum* 931 in lipids with different chemical compositions with (♦) vaseline, (■) paraffin, (▲) glycerolum, (x) olive oil, (*) Dimeticonum, (●) Akoline MCM, (▮) Akomed R, and (▬) Akorex L.

FIG. 5 shows the survival of *Lactobacillus plantarum* 931 in suspensions of water and olive oil with (♦) 10% olive oil in water and (■) 30% olive oil in water.

FIG. 6 shows transfer efficacy to and survival rate on skin of *Lactobacillus plantarum* 931 suspended in olive oil on hygiene tissues on five different subjects.

FIG. 7 shows transfer efficacy to and survival rate on skin of *Lactobacillus plantarum* 931 suspended in paraffin oil on hygiene tissues on five different subjects.

FIG. 8 shows transfer efficacy to and survival rate on skin of *Lactobacillus plantarum* 931 suspended in Milli Q water on hygiene tissues on five different subjects.

FIG. 9 shows transfer to and survival of *Lactobacillus plantarum* 931 suspended in olive oil in the urethra after application via a tissue sheet used in the urogenital area on four different subjects.

FIG. 11 shows the growth rate of *Lactobacillus plantarum* 931 cells after storage in olive oil on a tissue sheet (Δ and ○) as compared to the growth rate of freshly inoculated *L. plantarum* 931 cells from an overnight culture (■).

FIGS. 12-22 show perspective views of preferred embodiments of the design of a hygiene tissue according to the present invention.

DETAILED DESCRIPTION OF PREFERRED EMBODIMENTS

Figure 1:
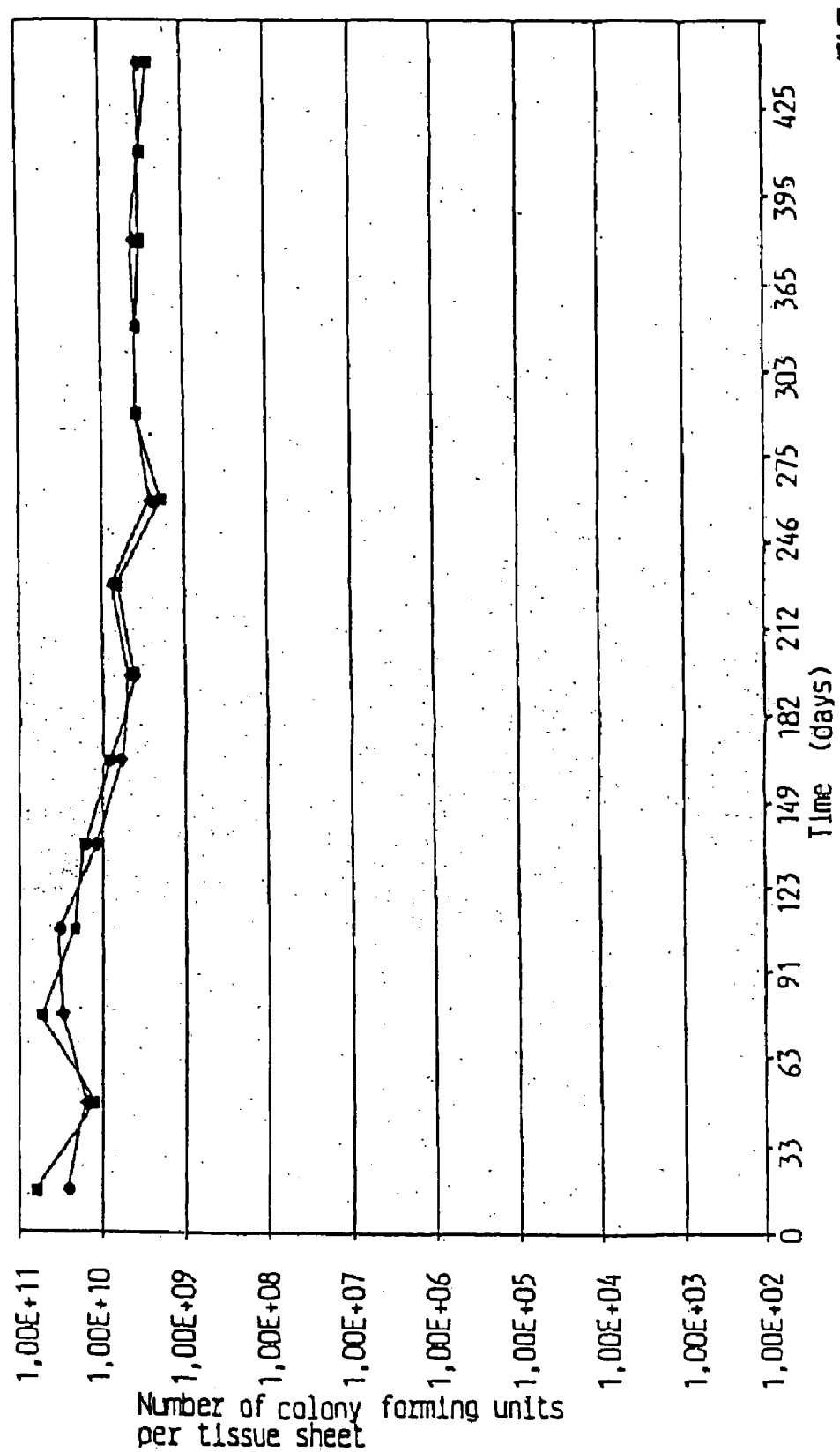
In FIGS. 1-9 1.00E+02 is $1.00 \times 10^2$, 1.00E+03 is $1.00 \times 10^3$, etc.

By "tissue" or "hygiene tissue" is meant any device for wiping skin, for instance, a washcloth, patch, towelette, napkin, wetwipe, and the like.

By "side" is meant the two sides indicated by the numbers 10 and 11 in e.g., FIG. 19, i.e., the sides are arranged on top of each other.

The term "section" refers to different zones on the hygiene tissue, where the sections are arranged side-by-side on the hygiene tissue, as indicated by the numbers 2 and 3 in, e.g., FIG. 12.

By "cleaning liquid" is meant a water solution, an oil-in-water emulsion, a water-in-oil emulsion or an oil, that can be used to clean the skin and the urogenital area.

By "matrix" is meant any natural or synthetic fiber, such as rayon, cellulose, regenerated cellulose, polyester, polyolefine fibers, textile and the like, or foam, nonwoven, felt or batting, or combinations thereof.

By "supplied" is meant that the cleaning liquid or bacterial composition is impregnated or coated onto the the hygiene tissue.

By "additional component" is meant agents commonly added to skin caring products, such as caring agents, water absorbent agents, pH buffering agents (weak organic or inorganic acids, such as lactic acid, ascorbic acid, citric acid or boric acid), perfume, antioxidants, hydrocortisone, other anti-inflammatory steroids, etc. Further details on suitable agents commonly added to skin caring products are given in *Harry's Cosmeticology 8th ed.*, Ed by MM Rieger, Chemical Publishing Co., Inc., New York, 2000. Additional component also encompasses agents enhancing bacterial performance such as antifreezing agents, such as skim milk, glucose, glutamate and glycerol, and nutrients, such as amino acids, peptides, nucleic acid derivatives, vitamins, salts, fatty acids, glucose, fructose, ribose, maltose and lactose.

By "barrier," "barrier sheet," or "barrier layer" is meant a material that prevents or reduces transfer/diffusion of cleaning liquid and/or bacterial composition between first and second parts of the hygiene tissue. The barrier material may be more or less pervious depending on the degree of prevention of transfer/diffusion of cleaning liquid or bacterial composition that is necessary.

By "lipid" is meant a water-insoluble organic molecule with a fatty character. Suitable lipids for the preferred embodiments of the present invention include petroleum-derived lipids, synthetic lipids, and animal- and plant-derived lipids.

Preferred "lactic acid producing bacteria" for the object of the present invention include bacteria from the genera *Lactobacillus, Lactococcus* and *Pediococcus*. Preferably the selected bacterium used is from the species *Lactococcus lactis, Lactobacillus acidophilus, Lactobacillus curvatus,* or *Lactobacillus plantarum*. Even more preferably, the lactic acid producing bacterium is *Lactobacillus plantarum* 931 (Deposition No. (DSMZ): 41918).

By "optional cleaning additive" is meant any agent commonly added to skin cleaning products, such as those chosen from the group of emollients, emulsifiers, moisturizers, pH-regulating agents, chelating agents, viscosity modifiers, antimicrobial agents, preservatives, nd fragances. Further details on suitable agents commonly added to skin cleaning products are given in *Woodruff's Ingredients and Formulary Handbook, John Woodruff, First ed.,* 1997, Miller Freeman UK Ltd.

The hygiene tissue provided in one embodiment of the present invention is intended to be used for cleaning and reestablishing and maintaining a healthy microbial flora on the skin and in the urogenital area. This is achieved by providing a hygiene tissue onto which a cleaning liquid and a composition comprising lactic acid producing bacteria are supplied to different parts of the tissue. When the hygiene tissue is used, the first part comprising the cleaning liquid is first used to clean the skin. Thereafter, the lactic acid producing bacteria are transferred to the skin using the second part of the hygiene tissue that comprises the lactic acid producing bacteria.

In one embodiment, the hygiene tissue provided can be composed of a matrix comprising any natural or synthetic fiber, such as rayon, cellulose, regenerated cellulose, polyester, polyolefine fibers, textile and the like, or foam, nonwoven, felt or batting, or combinations thereof. The tissue matrix preferably has a water content of 10% by weight or less, more preferably 5% by weight or less, most preferably 1% or less.

The hygiene tissue of an embodiment of the present invention combines two functions, i.e., cleaning of the skin and/or urogenital area and delivery of lactic acid producing bacteria, on the same hygiene tissue. The cleaning liquid and the bacterial composition are separated to at least two different parts of the hygiene tissue, thereby separating the two functions of the tissue. In one embodiment, the cleaning function of the hygiene tissue is provided via a cleaning liquid, which can be a water solution, an oil-in-water emulsion, a water-in-oil emulsion or an oil. The cleaning liquid can contain any commonly used water- or oil-soluble cleaning agent. The water-soluble cleaning agents are selected from the group of non-ionic, amphoteric and anionic surfactants. The oil-soluble cleaning agents are selected from the group of animal or plant-derived triglycerides, liquid hydrocarbons, such as paraffin oils, paraffin derivatives or mixtures thereof. The cleaning liquid is in an amount of 0.5-95% by the hygiene tissue's total weight, preferably between 5-50%. The cleaning liquid may further comprise one or more optional cleaning additives of the group of emollients, emulsifiers, moisturisers, pH-regulating agents, chelating agents, viscosity modifiers, antimicrobial agents, preservatives and fragrances.

The lactic acid producing bacteria on the hygiene tissue are preferably protected from moisture in order to survive during manufacture and storage of the tissue. Exposure to moisture during manufacturing and storage of products that comprise lactic acid producing bacteria may cause reactivation of the bacteria, which subsequently leads to their death. Therefore, by protecting the bacteria from moisture, their survival is enhanced and the durability of the product extended. The present inventors surprisingly found that by suspending the lactic acid producing bacteria in a form where the bacteria are in an environment with low water activity, such as dried, preferably freeze-dried, form, in one or more lipids, protected the bacteria from moisture, which resulted in enhanced bacterial survival. Suitable lipids for use to enhance the survival of lactic acid producing bacteria of the present invention support survival of the stored cells so that the maximum decrease in number of culturable cells is 3 log units after 12 months storage. More preferably, suitable lipids support survival of the stored cells so that the maximum decrease in number of culturable cells is 2 log units after 12 months storage, and most preferably, suitable lipids support survival of the stored cells so that the maximum decrease in number of culturable cells is 1 log unit after 12 months storage.

The inventors have also found that suspending bacteria in lipid results in enhanced transfer rates to the skin and urogenital area. This may be the result of the lipid having more adhesive properties than, for example, water, thereby resulting in a higher amount of bacteria actually being transferred to the skin. Suitable lipids enable transfer of bacteria to the skin of more $10^5$ or more culturable cells per $cm^2$. More preferably, suitable lipids enable transfer of bacteria to the skin of $10^6$ or more culturable cells per $cm^2$. Most preferably, suitable lipids enable transfer of bacteria to the skin of $10^7$ or more culturable cells per $cm^2$.

Also, the lipid has the effect of enhancing bacterial survival once the bacteria are delivered to the skin, presumably because of the lipid creating a micromilieu that is beneficial for retaining bacterial viability. Suitable lipids for use in embodiments of the present invention support survival of the bacterial cells on the skin so that $10^2$ or more culturable cells per cm$^2$ can be recovered 12 hours after delivery by use of the hygiene tissue. More preferably, suitable lipids support survival of the bacterial cells on the skin so that $10^3$ or more culturable cells per cm$^2$ can be recovered 12 hours after delivery by use of the hygiene tissue. Most preferably, suitable lipids support survival of the bacterial cells on the skin so that $10^4$ or more culturable cells per cm$^2$ can be recovered 12 hours after delivery by use of the hygiene tissue. Once the bacteria have been delivered to the skin, the moisture on the skin reactivates the bacteria, thereby allowing them to perform their intended action, i.e., competitively exclude and prevent colonization of pathogenic microbial species.

Examples of lipids suitable for embodiments of the present invention include petroleum-derived lipids, such as paraffinum liquidum (mineral oils, paraffin oils, and vaseline oils), petrolatum (vaseline and petroleum jelly), cera microcrystallina, ozokerite, ceresine and paraffins. Alternatively, synthetic lipids, such as dimethicone, cyclomethicone, and silicone esters, such as cetearyl methicone, can be used. A third alternative is to use animal- or plant-derived lipids, which usually are triglycerides. The animal- and plant-derived lipids are often mixtures of mono-, di- and triglycerides and free fatty acids. The lipids may be purified, hydrogenated, refined, modified, and used alone or in different mixtures. Examples of suitable, original animal-derived lipids include bees waxes, emu oil, lactic lapida, lanolin, shark liver oil, and tallow. Examples suitable of plant-derived original lipids include apricot kernel oil, arachis oil, avocado oil/wax, bayberry wax, black currant seed oil, borage seed oil, brazil nut oil, camelia sinensis oil, candelilla wax, canola oil, carnauba wax, castor oil, cocoa butter, coconut oil, corn oil, cotton seed oil, dog rose seed oil, evening primrose seed oil, grape seed oil, illipe butter, jasmine wax, jojoba wax, lavender wax, linseed oil, mango seed oil, olive oil, orange wax, palm oil, palm kernel oil, peanut oil, rice wax, safflower oil, sesame seed oil, shea butter, soybean oil, sunflower seed wax, sweet almond oil, and wheat germ oil.

Lipids suitable for an embodiment of the present invention preferably have a water content of 5% by weight or less, more preferably 3% by weight or less, most preferably 1% by weight or less.

Preferred lipids for the present invention include olive oil, canola oil, coconut oil, palm kernel oil, peanut oil, soy bean oil, dimethicone, paraffin oil, and petrolatum. These lipids are especially preferred since they provide high survival of lactic acid bacteria and high transfer rates of the bacteria to the skin and urogenital area. In addition, these lipids have positive effects in the skin; they have a soothing effect, show skin protective properties, and are non-toxic and non-allergenic. The preferred lipids are of non-animal origin.

Optionally, one or more additional components including caring agents, water absorbent agents (such as inorganic salts, e.g. calcium chloride), pH buffering agents (weak organic or inorganic acids, such as lactic acid, ascorbic acid, citric acid or boric acid), perfume, antioxidants, hydrocortisone and other anti-inflammatory steroids, can also be added to the hygiene tissue. These additional components are preferably added to the bacteria containing part of the hygiene tissue. Optionally, the bacteria containing part of the hygiene tissue can also comprise antifreezing agents, such as skim milk, glucose, glutamate and glycerol, alone or in different combinations. In addition, nutrients for bacterial propagation, such as amino acids, peptides, nucleic acid derivatives, vitamins, salts, fatty acids, glucose, fructose, ribose, maltose and lactose can be added, alone or in different combinations, to the bacteria containing part of the hygiene tissue.

The cleaning liquid containing part of the hygiene tissue can optionally be supplied with one or more optional cleaning additive(s). Examples of suitable cleaning additives include emollients, emulsifiers, tensides (non-ionic, amphoteric and anionic surfactants), moisturizers, pH-regulating agents, chelating agents, viscosity modifiers, antimicrobial agents, preservatives, and fragances.

In one embodiment, the number of probiotic bacteria on the hygiene tissue is preferably $10^4$-$10^{11}$ colony forming units (CFU) and more preferably $10^6$-$10^{11}$ CFU.

In one embodiment, the amount of lipid suspension of lactic acid producing bacteria on the tissue is 0.5-95% by weight.

In one preferred embodiment, the probiotic bacterial strain with antagonistic effect is selected from the genera *Pediococcus, Lactobacillus* or *Lactococcus,* or combinations thereof. In another preferred embodiment, the probiotic bacterial strain with antagonistic effect is at least a *Lactobacillus plantarum* strain. In an even more preferred embodiment, the probiotic bacterial strain with antagonistic effect is at least *Lactobacillus plantarum* 931 (deposition No. (DSMZ): 41918). The probiotic bacteria are preferably isolated from the skin or urogenital area of a healthy person. The preparation of probiotic bacteria are provided in a dried form, preferably as a freeze-dried powder. Preferably, the water activity of the bacterial preparation is 0.30 or less, more preferably 0.25 or less, most preferably 0.20 or less.

The design of the hygiene tissue is important for the present invention. It is preferable that the cleaning liquid and the bacterial composition are not mixed on the tissue in order to keep the cleaning and lactic acid bacteria transferring functions separated. Also, it is preferable to protect the bacteria from the cleaning liquid in order for the cleaning liquid not to interfere with bacterial survival via the presence of any moisture or agents with antimicrobial in the cleaning liquid. This is particularly preferable when a water-based cleaning liquid is used, since contact of the bacteria with water decreases bacterial survival. Therefore, the hygiene tissue of an embodiment of the present invention is composed of (i.e., divided into) at least a first and a second part. In order to separate the different parts and functions of the tissue from each other, a barrier can optionally be placed between the different parts of the tissue, as indicated in the preferred embodiments below. The preferred materials for a barrier are chosen depending on the degree of imperviousness that is required in each specific case, depending on the design of the tissue and the cleaning liquid used. For example, a more water impervious barrier may be used if a water-based cleaning liquid is used, rather than if an oil-based cleaning liquid is used. In contrast, no barrier may be necessary if an oil-based cleaning liquid is used. Materials suitable to use as barrier include polyethylene, polypropylene, polyester, polyamide, polyvinylalcohol and similar polymers, but other materials such as aluminium foil, and the like can also be used as barrier material. The barrier can also be comprised of wax(es) and other water repellant materials added to the hygiene tissue in the region between the differents parts of it. The different parts of the hygiene tissue can be made of the same tissue matrix or different matrices and the cleaning liquid and bacterial composition can be applied to the whole of a part of the hygiene tissue or just a portion.

In order to facilitate for the user to distinguish which part of the hygiene tissue that comprises the cleaning liquid and the bacterial composition, respectively, a visual indicator can be optionally added to one or both of the parts of the hygiene tissue. Suitable visual indicators for the present invention include dyes commonly used in the cosmetical, pharmacological and food industry. Examples of such dyes are included in the groups of nitro-, monoazo-, diazo-, ftalocyanin-, quinolin-, xanten-, triarylmethane-, indigoid- and vegetabilic dyes.

The geometrical shape of the hygiene tissue is not critical for the present invention and any form, e.g., rectangular, circular, irregular, etc., is possible. Some examples of preferred designs of the hygiene tissue are presented below that allow the cleaning liquid part and the bacterial composition part of the hygiene tissue to be separated. However, these examples are only for illustrative purposes and are not intended to limit the scope of the invention. In the figures the same numerals are used to describe similar parts of the hygiene tissue in some of the different embodiments.

FIG. 12 is a side perspective view, which shows a first preferred embodiment of a hygiene tissue 1 according to the present invention. In this embodiment, the hygiene tissue comprises a first and a second part of tissue matrix arranged in different sections, wherein the first part 2 is supplied with a cleaning liquid and the second part 3 is supplied with the bacterial composition. The first and second parts are arranged side by side, and may constitute two parts of the same tissue matrix, having different impregnation, or may be separate sheets joined together.

As shown in FIG. 13, a barrier 4 may be placed in the joint area between said first part 2 and second part 3 extending along the joint between the first and second parts. The height of the barrier is at least the same as the thickness of the tissue matrix of the first part 2 and second part 3, thus making the barrier an integrated part of the hygiene tissue.

Figure 14A:
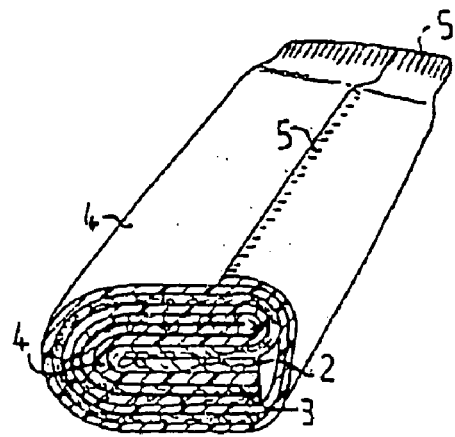
Figure 14B:
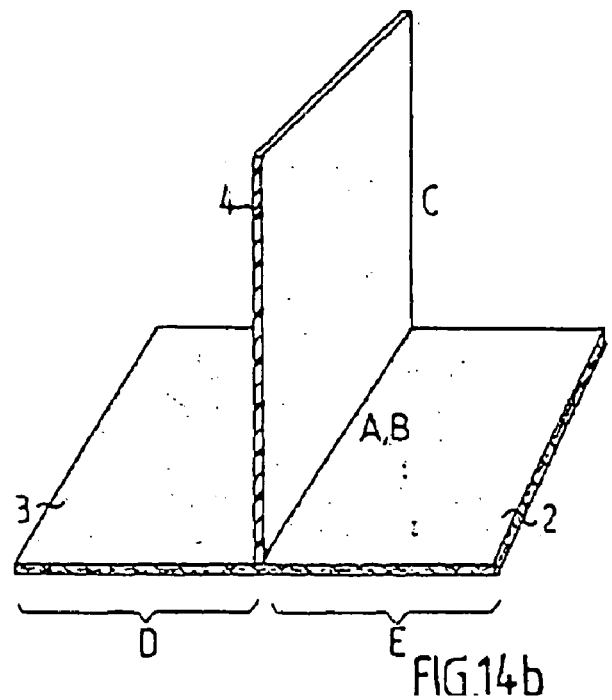

The first part 2 and the second part 3 are preferably separated by a barrier. In one variant shown in FIGS. 14*a-b*, showing the folded (14*a*) and the unfolded (14*b*) variant, the barrier is in the form of a barrier sheet 4. The barrier sheet is arranged in such a manner that it extends outwards from the joint between the first part 2 and second part 3 (FIG. 14*b*). The barrier sheet preferably has a width (A), at least substantially corresponding to the length (B) of joint between the first and second parts of the hygiene tissue, and a length (C), at least corresponding to the length of one of said first or second parts (D, E). Accordingly, the barrier sheet extends over substantially the whole area of at least one of said first or second parts, thus separating the first and second parts from each other, when the hygiene tissue is folded. Preferably, the length of the barrier sheet is at least 1.5 times the total length of the hygiene tissue. This enables the barrier sheet 4 to be folded around the hygiene tissue, thus to provide both a barrier between the first part 2 and second part 3 and a package at the same time (FIG. 14*a*). The barrier sheet is, when folded as a package, preferably sealed at its outer edges 5 by welding or use of an adhesive, thus completely enclosing the hygiene tissue, and is to be ripped open by the user. FIG. 14*a* discloses a schematic perspective view, partly in section, of such a package. Preferably the barrier sheet has a greater length and/or width than the first part 2 and second part 3 so that in the folded condition the outer edges of the barrier sheet can be sealed together without the seal affecting the first part 2 and second part 3. The barrier sheet may be attached at the joint between the first part 2 and second part 3 and extending outwards from the joint. Alternatively, the barrier 4 may be a separate sheet, which is placed inside the folded hygiene tissue and wrapped around it.

The hygiene tissue according to the variant shown in FIG. 13 is advantageously laminated with an additional layer 6, as shown in FIG. 15. Materials suitable for the additional layer include polyethylene, polypropylene, polyester, polyamide, polyvinyl alcohol and similar polymers, but other materials such as aluminium foil, and the like can also be used. The additional layer preferably cover both said first part 2 and second part 3 of the hygiene tissue, that optionally are separated by a barrier 4, and may extend from the hygiene tissue. The additional layer preferably also comprises a side flap 7, which has at least such dimensions that it can cover the entire hygiene tissue and thus completely enclose the hygiene tissue, when folded around the hygiene tissue, thereby forming a package for the hygiene tissue, as shown in FIG. 16. The side flap 7 can be an extension of the additional layer or a separate part. If the side flap 7 is a separate part, the edges of the side flap 7 are sealed together with the edges of the hygiene tissue and/or the laminated additional layer, by welding or using an adhesive. The edges of the folded package shown in FIG. 16 are preferably welded or sealed by using an adhesive thereby forming a seal.

In a further variant, shown in FIGS. 17 and 18, the additional layer is provided with two side flaps 8 extending outwards from the edge of the first part 2 and the second part 3 of the hygiene tissue, respectively. The side flaps 8 can be separate parts or an extension of the additional layer 6. The dimensions of the side flaps are such that each side flap can cover one of said first part 2 or second part 3 of the hygiene tissue. If the side flaps 8 are a separate part the side edges of the side flaps are preferably sealed together with the corresponding edges of the hygiene tissue and/or the additional layer 6. The side flaps are folded over the hygiene tissue, so that their external edges meet in the area above the barrier 4. The external edges of the side flaps are preferably sealed together in the area above the barrier 4, and/or are sealed to the barrier 4, and sealed to the edges of the tissue, by welding or using an adhesive, thus forming a package for the hygiene tissue. In this variant, the side flaps can be opened or removed one at a time. Thereby, the part of the hygiene tissue comprising the bacterial composition is protected by a side flap while the part of the hygiene tissue that comprises cleaning liquid is used for cleaning. Thereby, the bacterial part is not contaminated by the cleaning liquid or dirt removed from the skin before it is used.

FIG. 19 is a side perspective view of a another preferred embodiment of a hygiene tissue according to the present invention. In this embodiment, the first part 10, which is supplied with a cleaning liquid, is laminated with the second part 11, which is supplied with a bacterial composition, both parts having substantially the same surface extension and being arranged on different sides of the hygiene tissue. The first part 10 and second part 11 are optionally separated by a barrier layer 12, which is laminated between said first part 10 and second part 11, said barrier layer extending between the first part 10 and second part 11 over their entire surface. The hygiene tissue of this embodiment is preferably provided with a first side flap 13 and a second side flap 14 on two opposite edges of the hygiene tissue, as shown in FIG. 20. The first side flap 13 and the second side flap 14 are folded in different directions so that that they each cover one of said first part 10 or second part 11 of the hygiene tissue, respectively. The side flaps may be sealed at their edges, thus forming a package for the hygiene tissue. Also in this variant, the side flaps can be opened or removed one at a time. Thereby, the part of the hygiene tissue comprising the bacterial composition is protected by a side flap while the part of the hygiene tissue that comprises cleaning liquid is used for cleaning. Thereby, the bacterial part is not contaminated by the cleaning liquid or dirt removed from the skin before it is used. In the embodiments described in FIGS. 19 and 20, the bacterial suspension and/or cleaning liquid can also be directly applied to the barrier.

Figure 21:
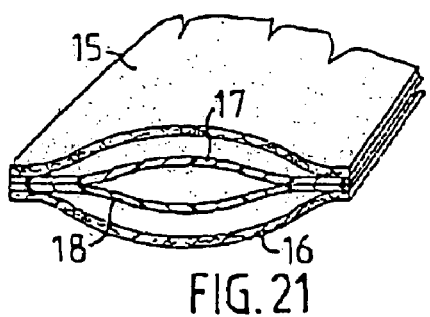

A third preferred embodiment of the hygiene tissue according to the present invention is shown in FIG. 21. The first part comprises a first tissue sheet 15 and the second part comprises a second tissue sheet 16 arranged on top of each other, one part being supplied with the cleaning liquid and the other with the bacterial composition. The first part 15 and the second part 16 are not laminated, but are joined at two opposite side edges, and optionally at a third edge, to form a tube or bag structure. The first part 15 and the second part 16 can also be constituted of the same tissue sheet being folded and sealed as to form a tube or bag structure. In this design, the hygiene tissue may function as a "washing glove." A barrier sheet 17, having the same surface extension as the first and second parts, is preferably arranged between said first part 15 and second part 16 thus separating them. The hygiene tissue is advantageously provided with a second barrier sheet 18 arranged below the first barrier sheet 17. The barrier can also be constituted of a single barrier sheet being folded as to form the tube or bag structure. By this arrangement, the user's hand does not need to come in contact with the cleaning liquid or the bacterial composition, since he/she may hold the hygiene tissue between the first barrier sheet 17 and the second barrier sheet 18. The first barrier sheet 17 and the second barrier sheet 18 may also be laminated to the first part 15 and second part 16, respectively. In the embodiments described in FIG. 21 the bacterial suspension and/or cleaning liquid can also be directly applied to the barrier instead of being impregnated onto the tissue matrix.

Figure 22:
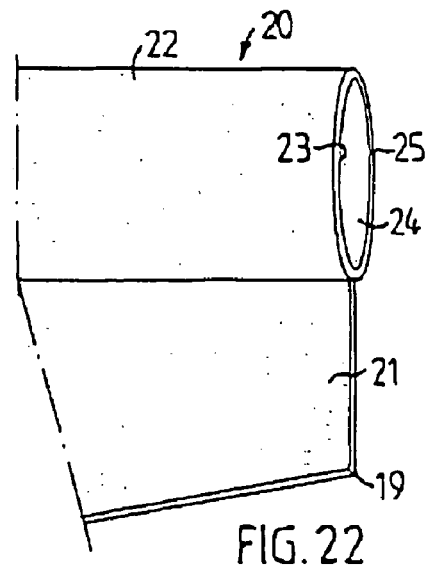

In another embodiment, shown in FIG. 22, the first part of the hygiene tissue, which is supplied with a cleaning liquid, is arranged as a side flap 19. The second part 20 comprises a first tissue sheet 22 and a second tissue sheet 24 sealed to form a tube or bag structure. The second part 20 can also be comprised of a single tissue sheet folded and sealed to form a tube or bag structure. The side flap 19 is initially folded over the first sheet 22 of the second part 20 of the hygiene tissue, which is supplied with a bacterial composition. Preferably, the side flap 19 is laminated with a barrier sheet 21 protecting the part of the hygiene tissue comprising the bacterial composition from contact with the first sheet 22 of the second part 20 of the hygiene tissue when the side flap 19 is folded over the second part 20. After having used the first part containing the cleaning liquid, the side flap 19 can be ripped of by the user or folded away from the hygiene tissue, in order to expose the sheet 22 containing the bacterial composition. The opposite side 24 of the tube or bag to the side containing the bacterial composition, may be a sheet of any appropriate material and may or may not contain a bacterial composition. If preferred, the second part of the hygiene tissue comprising the bacterial composition may also comprise a first protective sheet 23 and optionally a second protective sheet 25 placed inside the tube or bag structure. The first protective sheet 23 and the second protective sheet 25 may or may not be laminated to the first sheet 22 and the second sheet 24, respectively. The first protective sheet 23 and the second protective sheet 25 can also be constituted of the same protective sheet folded to form the tube or bag structure. Preferably, the protective sheet is composed of the same material as is suitable for the barrier, as described above. The hygiene tissue depicted in FIG. 22 can also be constituted of a single tissue sheet being folded and having its edges sealed as to form the structure of a tube or bag structure with a side flap.

In all the preferred embodiments described above, the different parts of the hygiene tissue may be constituted of the same or different tissue matrices.

The hygiene tissues according to an embodiment of the invention can either be individually packed or provided in a dispenser. As described above, the package can also be an integrated part of the hygiene tissue.

EXAMPLES

Example 1

Survival of *Lactobacillus Plantarum* 931 in Olive Oil on Hygiene Tissues

A preparation of freeze dried *L. plantarum* 931 cells in skimmilk was grounded until a powder of fine grains was formed. 10 g of the *L. plantarum* 931 powder was added to 120 ml olive oil (Filippo BERIO extra virgin olive oil) and shaken until a homogenous solution was formed. An additional aliquot of 80 ml of olive oil was added and the resulting 200 ml solution was vortexed for ca 2 min. The bacterial suspension was kept at room temperature for 3 hours, with mixing twice an hour. Tissue sheets (Spun Lace Dupont and SCA Absbond) were cut to 6×4 cm squares and placed in sterile stainless steel trays. On each tissue sheet, 2 ml of bacterial suspension was dropped over the tissue to cover it. The tissue sheet was folded in the middle, then from the long side to the middle again and packed in foil bags, which edges were welded. Samples were removed for determination of initial bacterial concentration and the remaining bags were stored at room temperature for viability studies.

As a comparison to storage of *L. plantarum* 931 cells in olive oil, *L. plantarum* 931 cells were stored in suspensions of water and olive oil. These were prepared by mixing vigorously 2.5 g of freeze dried *L. plantarum* 931 cells (prepared as described above) with 45 ml of Milli Q water and 5 ml olive oil (Filippo BERIO, Italy) or 35 ml Milli Q water and 15 ml olive oil to prepare suspensions with approximately 10 or 30% oil, respectively. The bacterial oil-water suspensions were applied to tissue sheets (Spun Lace Dupont) for bacterial survival studies. On each tissue sheet (6×7 cm), 1 ml of bacterial suspension was dropped to cover the tissue. The tissue sheet was folded in the middle, then from the long side to the middle again and packed in foil bags, which edges were welded. Samples were removed for determination of initial bacterial concentration and the remaining bags were stored at room temperature in the dark for viability studies.

To test the viability of the *L. plantarum* 931 cells after storage for different time periods on a tissue sheet, the tissue sheet was transferred to a Stomacher bag and 10 ml of 0.9% NaCl was spread over the tissue sheet. The bag was run for 3 min on high effect in Stomacher. The contents of the bag was then transferred to test tubes, diluted in 0.9% NaCl when necessary, and immediately plated onto Rogosa plates. The number of colonies was counted after 2 days of incubation at 37° C. in 5% $CO_2$ in air. Two tissue sheets were analyzed at each sampling date.

Figure 2:
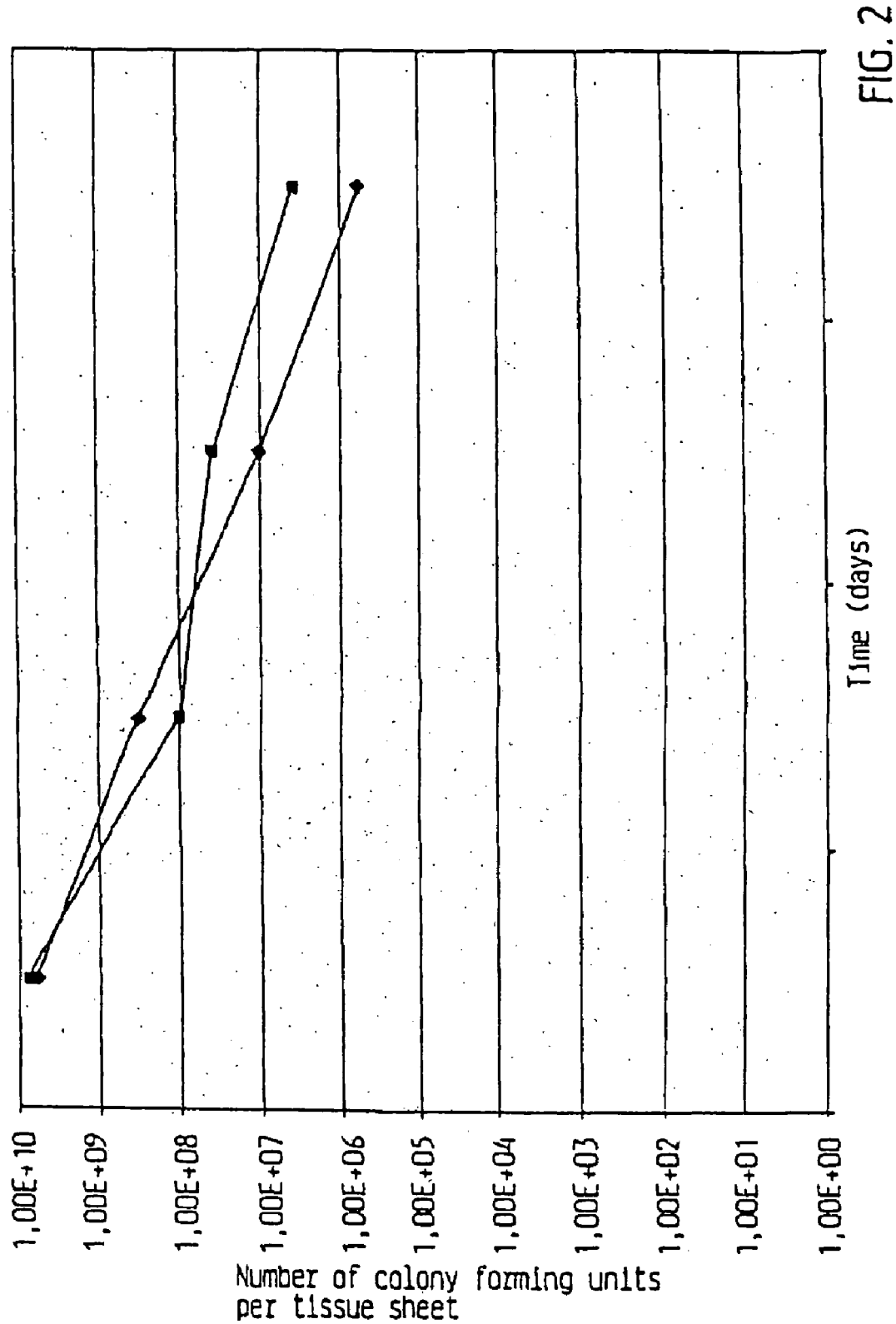

The survival of *L. plantarum* 931 in olive oil for a total time period of one year and three months is shown in FIG. 1. The survival of the *L. plantarum* 931 cells stored under these conditions was very high for both tissue sheets variants tested. In comparison, storage of oil-water suspensions (10 and 30% olive oil in water) of the bacteria on a tissue sheet (FIG. 2) resulted in a rapid decrease in viability with a drop of more than $10^3$ orders of magnitude over just a three months time period studied.

Example 2

Survival of L. Plantarum 931 in Lipids with Different Chemical Compositions 497 mg of a powder of L. plantarum 931 in skim milk, prepared as described in Example 1, was mixed with 5 ml of olive oil (Filippo BERIO extra virgin olive oil, Filippo BERIO, Italy) or rapeseed oil (Felix AB, Sweden). The pH of the oils was about 5. The rapeseed oil also contained citric acid and vitamin A and D. The suspensions were vortexed for 1 min and allowed to rest for 1 min. This was repeated four more times. The bacterial suspensions were kept for 4 hours at room temperature with mixing twice an hour. The suspensions were then divided into 1 ml aliquots and stored in sterile brown glass vials. The initial concentrations of bacteria in the suspensions were determined. The vials were stored in a dark place at room temperature and normal air humidity varying from 30-60%.

In addition to the experiment described above, to further compare the survival of L. plantarum 931 in lipids with different compositions, 2 g of freeze-dried L. plantarum 931 cells in skimmilk ($2 \times 10^{10}$ colony forming units/g) were mixed with either 40 ml or 40 g of the different lipid compositions, depending on the lipid consistency. The tested lipids were: white vaseline (petrolatum, Apoteket AB, Umea, Sweden), paraffin (paraffinum liquidum, Apoteket AB, Gothenburg, Sweden), glycerol ("glycerin," maximum water content 0.5%, Apoteket AB Gothenburg, Sweden), olive oil ("Olea Europea," cold pressed, Apoteket AB, Gothenburg, Sweden), dimethiconum (Dimethicone, 350 cSt., Dow Corning 200/350 S fluid, Kebo Lab, Sweden), and Akoline MCM (mono-diglyceride of medium chain fatty acids; primarily caprylic and capric acids, Karlshamns AB, Sweden), Akomed R (caprylic/capric triglyceride from coconut and/or palm kernel oils, deodorized, Karlshamns AB, Sweden), and Akorex L (canola oil, partially hydrogenated, deodorized, Karlshamns AB, Sweden). The samples were stored in sterile, brown, glass vials at room temperature in the dark at normal air humidity (varying from 30-60% relative humidity). To establish the number of viable L. plantarum 931 cells after different storage times, 1 g of the samples was transferred to a stomacher bag and 9 ml of 0.9% NaCl was added. The bag was then run at high effect in Stomacher for 3 min. The contents of the bag was transferred to test tubes, diluted when necessary in NaCl and cultured on MRS-plates at 37° C. in 5% $CO_2$ in air for 2 days.

As a comparison to storage of L. plantarum 931 cells in different lipids, L. plantarum 931 cells were also stored in suspensions of water and olive oil. These were prepared by mixing vigorously 2.5 g of freeze dried L. plantarum 931 cells (prepared as described above) with 45 ml of Milli Q water and 5 ml olive oil (Filippo BERIO, Italy) or 35 ml Milli Q water and 15 ml olive oil to prepare suspensions with approximately 10 or 30% oil, respectively. The samples were stored in sterile plastic vials at room temperature at normal air humidity (varying from 30-60% relative humidity). To test survival after different time intervals, samples were removed from the vials, diluted in 0.9% NaCl and incubated at 37° C. in 5% $CO_2$ in air for 2 days.

Figure 3:
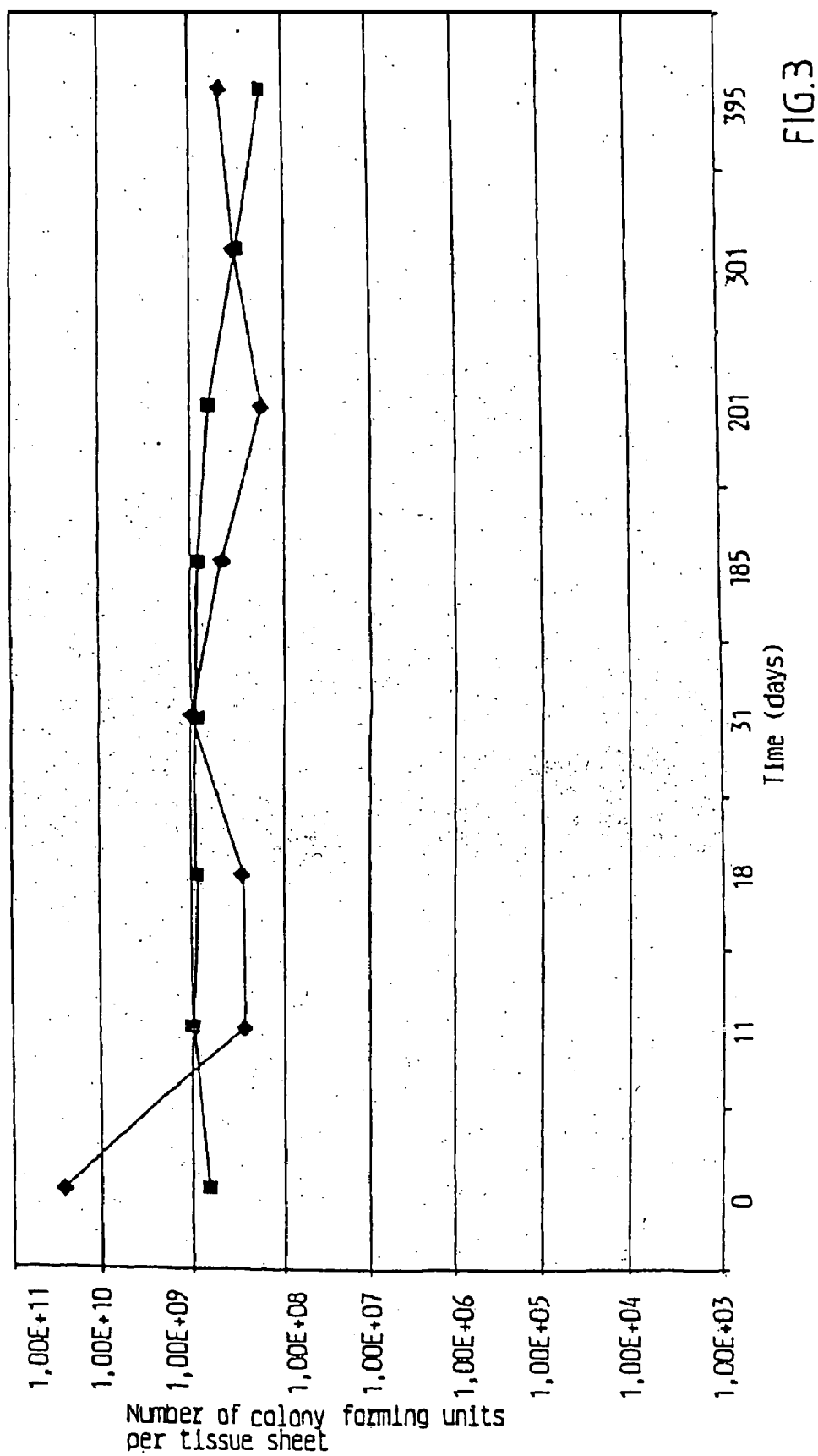
Figure 4:
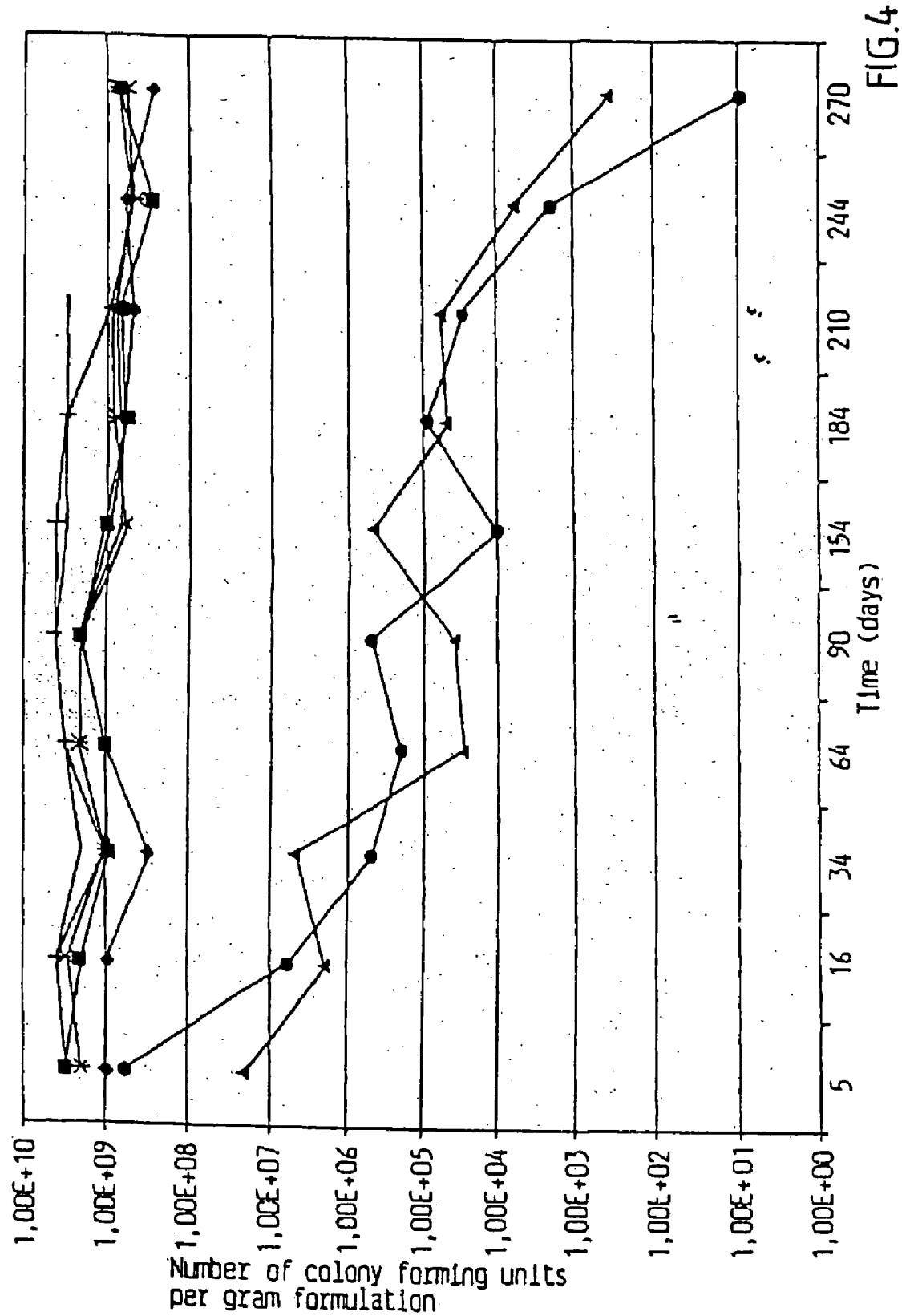
Figure 5:
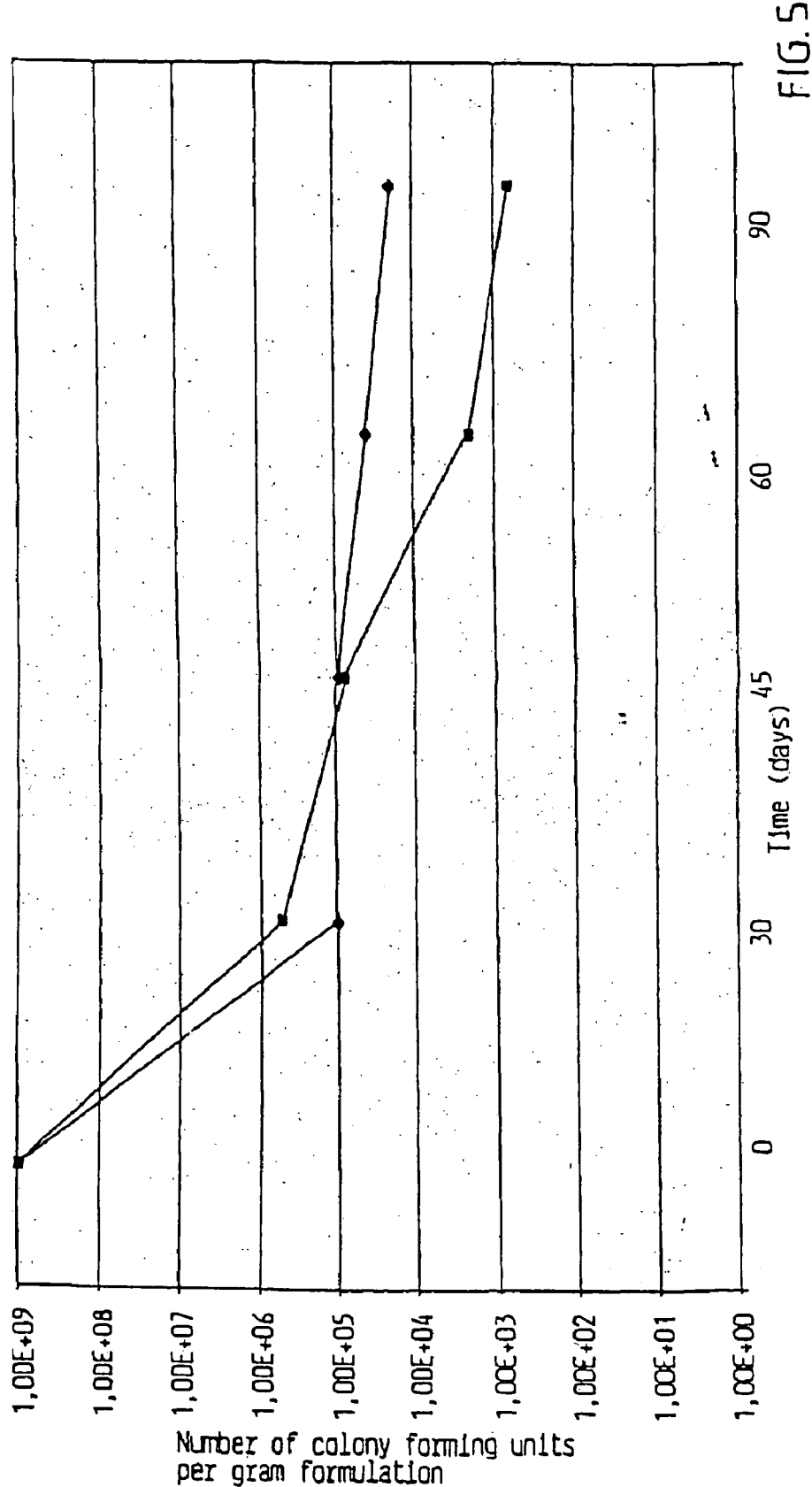

FIG. 3 shows an extraordinarily high level of survival of the L. plantarum 931 cells in olive and rapeseed oil over the more than one year time period studied. Storage in vaseline, paraffin, Dimeticonum, Akoline MCM, Akomed R, and Akorex L also resulted in a high survival over extended time periods (FIG. 4). However, storage in the more hydrophilic glycerol resulted in a pronounced decrease in survival over time (FIG. 4). Also, the Akoline MCM, known to have bacteriostatic properties, could not support survival of the cells (FIG. 4). In addition, it can be seen that storage in the more hydrophilic environment provided in the oil-water suspensions (FIG. 5) results in a very rapid initial decrease in viability by more than $10^2$ orders of magnitude over the first month of storage. During the next two months studied, the decrease in survival rates flattened out, but still the decrease in survival is much higher than what is observed when the bacterial cells were stored in a lipid.

Example 3

Study on Transfer Efficacy to and Survival Rates on Skin of L. Plantarum 931 Suspended in Olive Oil, Paraffin Oil or Milli Q Water 2.00 g of freeze-dried L. plantarum 931 were added to a sterile glass vial and 40 ml of olive oil, paraffin oil or Milli Q water were added. The suspensions were shaken until homogenous solutions formed and were left at room temperature for four hours. Tissue sheets with L. plantarum 931 were prepared by cutting tissue sheets to 7×8 cm pieces and dropping 2 ml of the different bacterial suspensions, prepared as described above, to cover the tissue. The tissue sheets were folded in the middle, then from the long side to the middle again and packed in foil bags which edges were welded. Samples were removed for determination of initial bacterial concentrations and the remaining bags were stored at room temperature for viability studies. Two of the prepared tissue sheets with L. plantarum 931 for each preparation were used in the bend of the arm on five subjects (i.e., one tissue was used for three subjects and the other one for two). Before the test, samples were taken to assure that no L. plantarum 931 cells were initially present on the skin. On each subject in one bend of the arm, a tissue sheet with L. plantarum 931 in Milli Q water was streaked and a tissue sheet with L. plantarum 931 in olive oil was similarly used in the other. The skin was then sampled for presence of L. plantarum 931 cells at 0, 4, 6 and 24 hours after streaking. The sampling procedure was as follows: a sterile stick provided with a cotton wool top was dipped in 0.9% NaCl and rolled 4 times over an area of 1 $cm^2$ at the site of application of the bacteria. The stick was then dipped in 1 ml of 0.9% NaCl and mixed. The samples were diluted in 0.9% NaCl and immediately plated onto Rogosa plates. The plates were incubated at 37° C. in 5% $CO_2$ in air for 2 days. After 24 hours the bend of the arm, where L. plantarum 931 cells in Milli Q water were applied, was rinsed with Sumabac (Diversey Lever, Huddinge, Sweden) and a tissue sheet with L. plantarum 931 cells in paraffin oil was streaked in that bend of the arm, which, as previously, was sampled at 0, 4, 6 and 24 hours after streaking to assess the amount of L. plantarum 931 cells on the skin.

Figure 6:
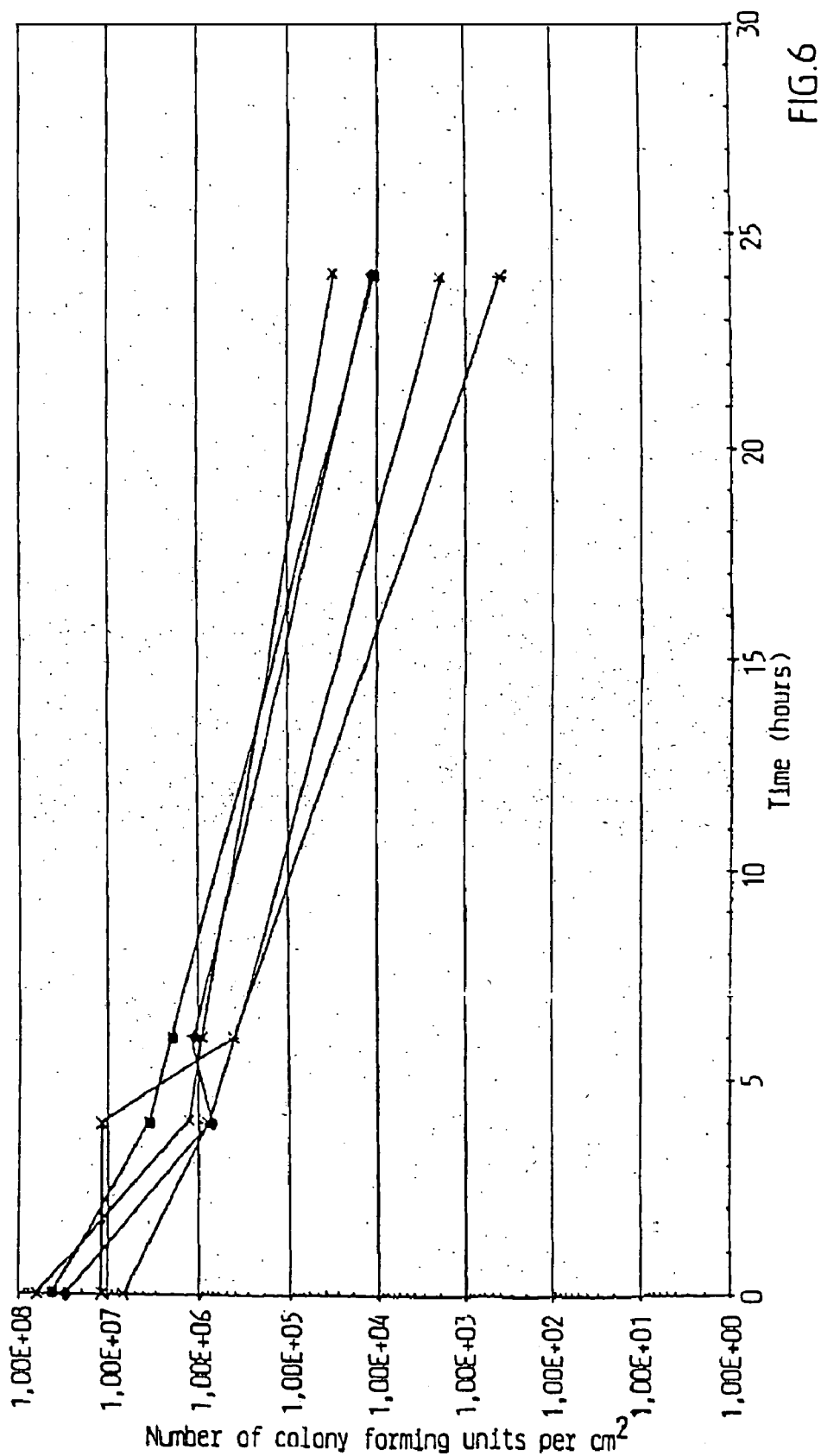
Figure 7:
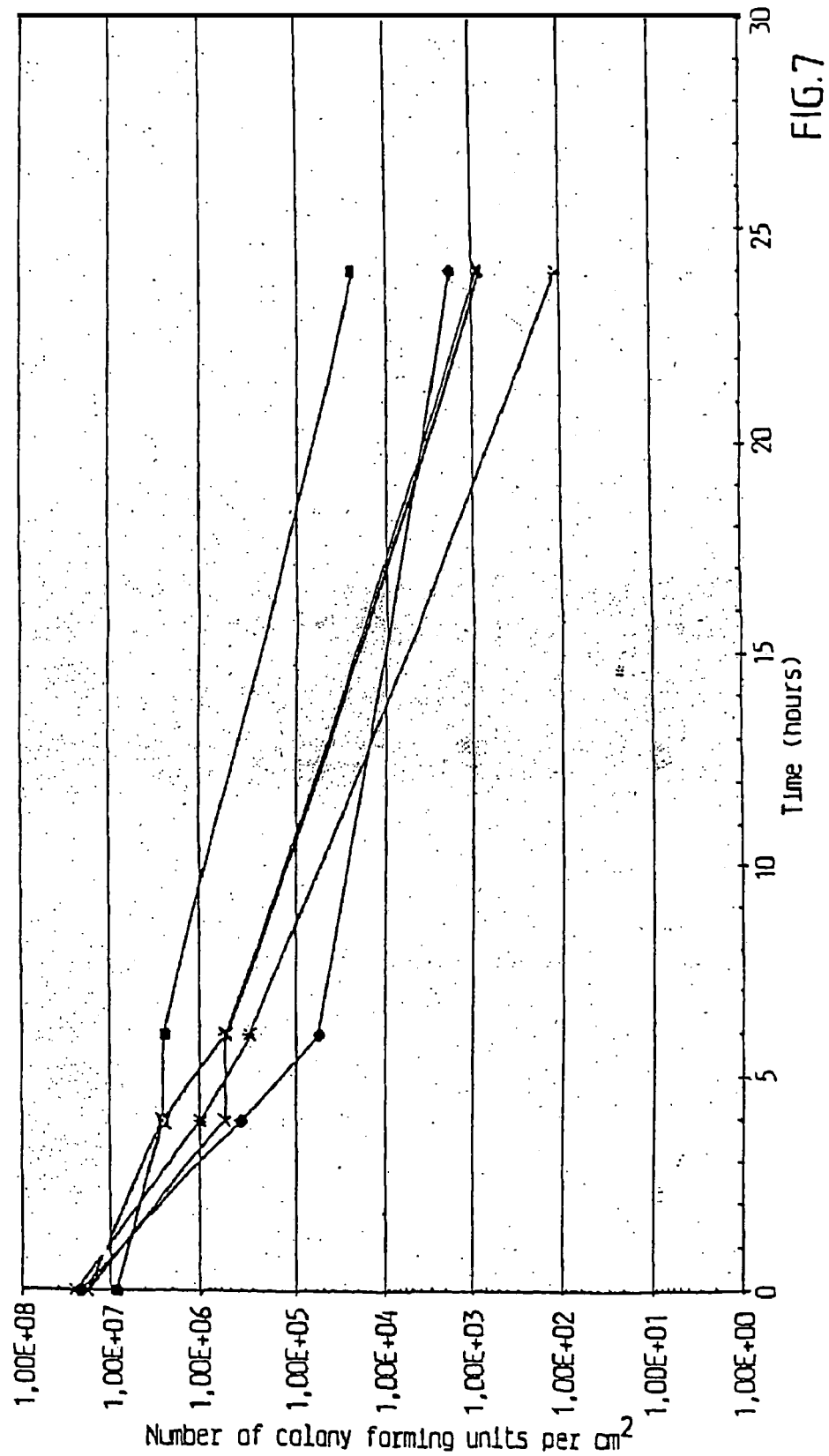
Figure 8:
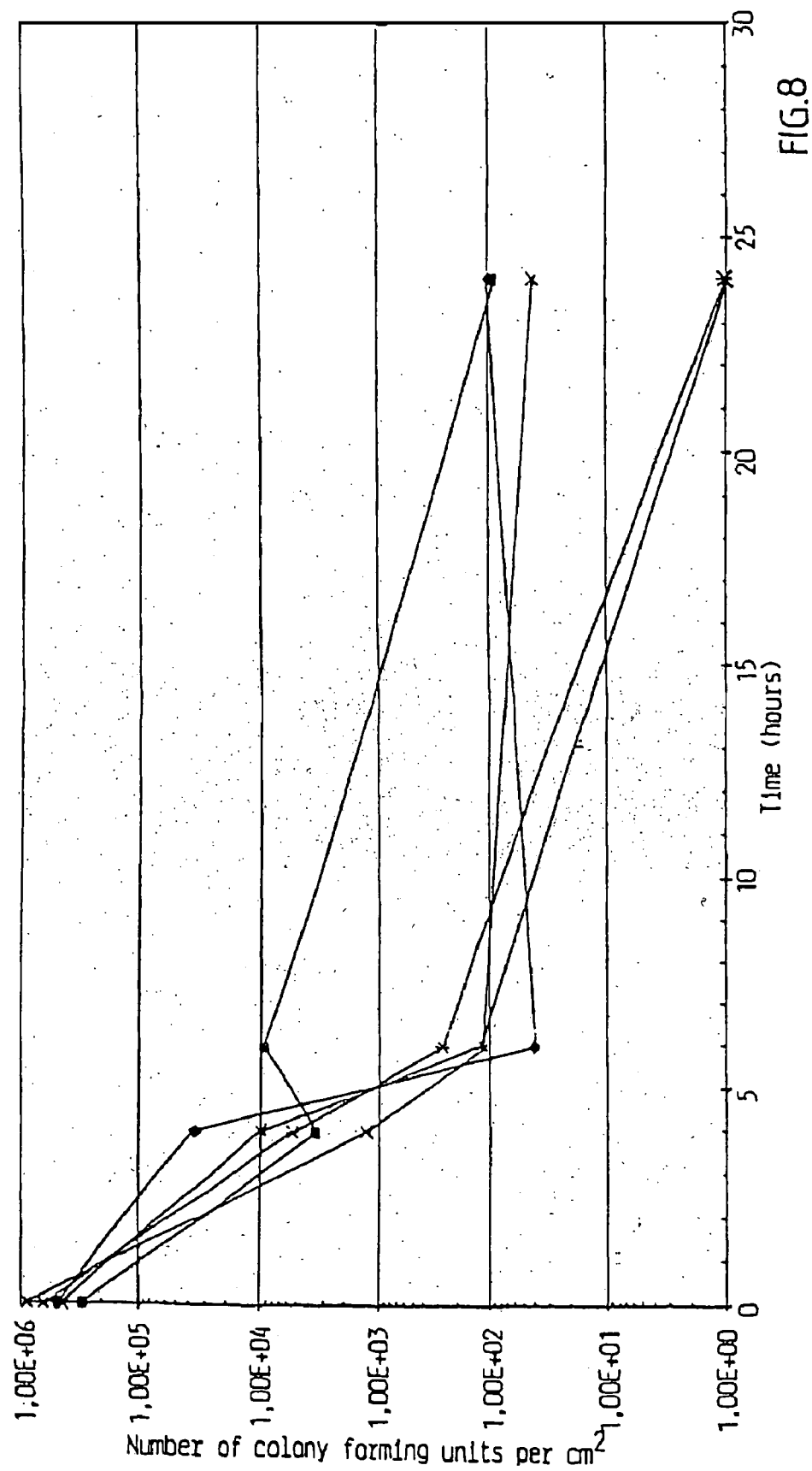

As shown in FIGS. 6-8 the amount of L. plantarum 931 cells transferred to the skin was usually more than 10 times higher when the bacteria were suspended in olive (FIG. 6) or paraffin oil (FIG. 7) compared to when they were suspended in Milli Q water FIG. 8). Suspending the bacteria in lipid instead of water therefore was demostrated to enhance the transfer rate of the bacteria to the skin. Also, once the L. plantarum 931 cells were on the skin, the lipid also enhanced bacterial survival, since the initial drop in bacterial counts was slower and the final level of bacteria on the skin after 24 hours was much higher after use of a tissue where the bacteria were suspended in olive or paraffin oil (FIGS. 6 and 7), compared to what was found when water was used as suspending agent (FIG. 8).

Example 4

Transfer of *L. Plantarum* 931 Suspended in Olive Oil Applied to a Tissue Sheet Used in the Urogenital Area A bacterial suspension was prepared by adding 5.051 g of a powder of *L. plantarum* 931 (prepared as described in Example 1) to 100 ml olive oil (Filippo BERIO extra virgin olive oil). The powder was first added to 75 ml of olive oil and shaken to form a homogenous solution before addition of another 25 ml, followed by vortexing for 2 min. The bacterial suspension was kept at room temperature for 2 hours, with mixing twice an hour. A tissue sheet was prepared and inoculated with the bacteria as described in Example 1. Four girls were treated with the tissue sheet in the urogenital area. Samples were collected from the urethra and perineum, using sterile cotton sticks, before using the tissue sheet, to ensure that no lactobacilli were initially present. Thereafter samples were collected immediately after treatment, and after 2, 4, 6, and 17 hours, to monitor transfer and survival of the lactobacilli by dipping a sterile stick provided with a cotton wool top in MRS-broth and rolling it three times over an area of 1 cm$^2$ at the site of application of the bacteria. The stick was then put in one ml MRS-broth. In the same way a stick was rolled over the uretra over an area of ¼ cm$^2$ and was the put in another tube of MRS-broth. The samples were plated onto Rogosa plates containing 128 mg/ml vancomycin. The plates were incubated at 37° C. in 5% $CO_2$ in air for two days.

Figure 9:
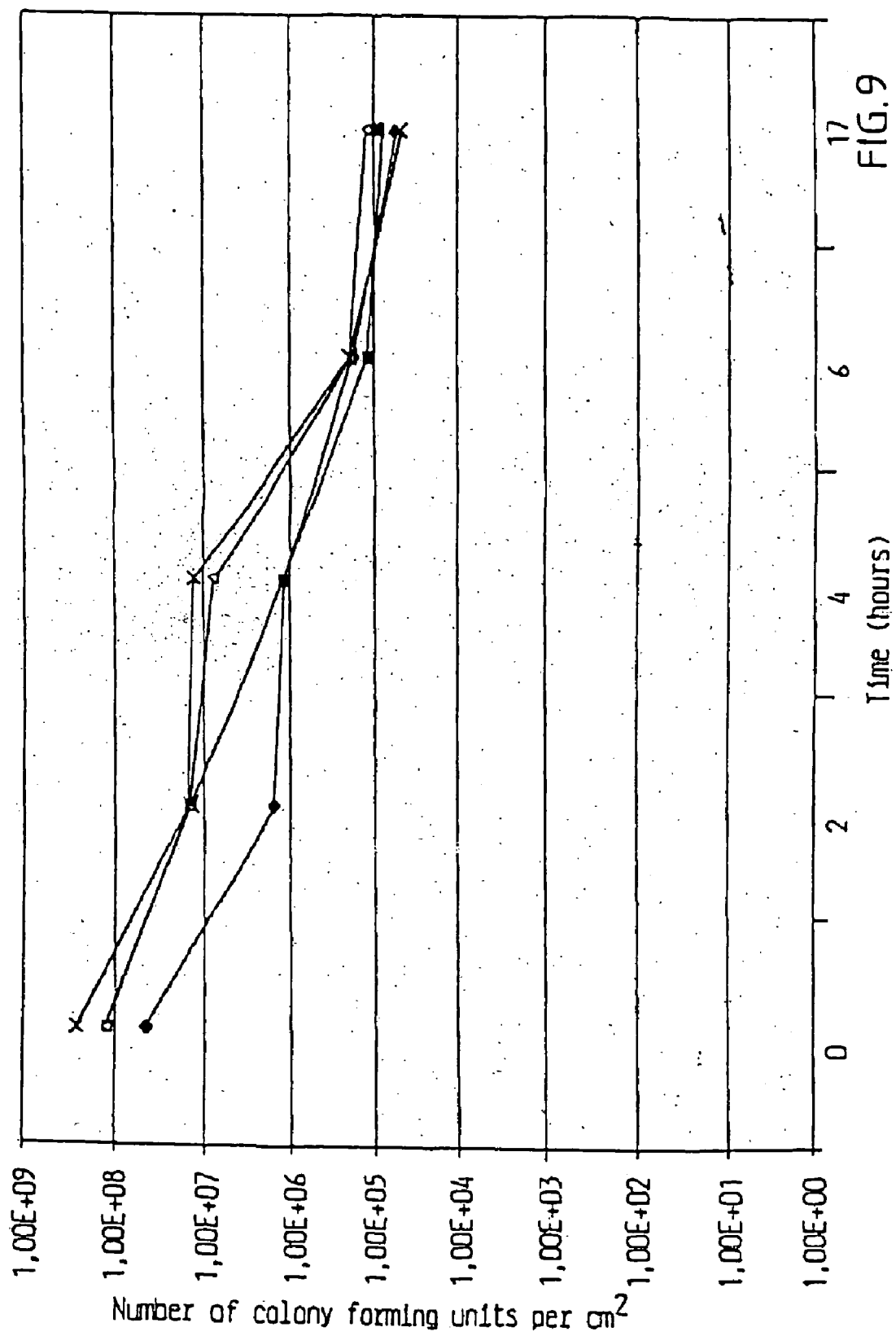
Figure 10:
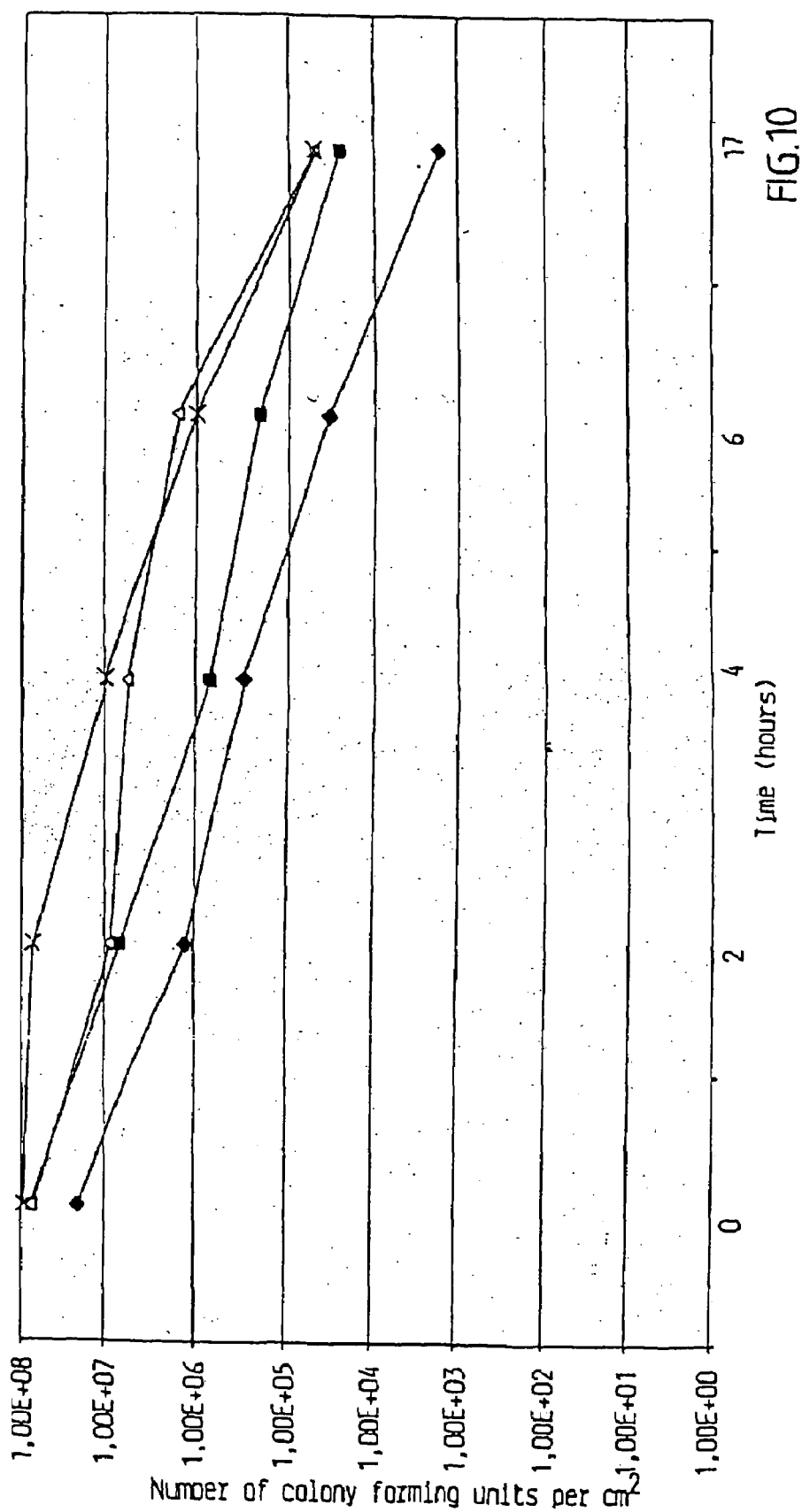
FIG. 10 shows transfer to and survival of *Lactobacillus plantarum* 931 suspended in olive oil in the perineum after application via a tissue sheet used in the urogenital area on four different subjects.

The girls were not allowed to take a bath or shower during the study, but were not given instructions in any other respect. The results shown in FIGS. 9 and 10 demonstrate that there was a high level of transfer of *L. plantarum* 931 to the urethra (FIG. 9) and perineum (FIG. 10) and that a surprisingly high amount of bacteria remained in these areas during the time period studied.

Example 5

Viability of *L. Plantarum* 931 After Storage in Olive Oil on a Hygiene Tissue Growth of *L. plantarum* 931 suspended in olive oil on tissue sheets that had been stored for 6 days was compared to growth of *L. plantarum* 931 that were not suspended and stored in olive oil. The tissue sheets were wetted with 10 ml 0.9% NaCl and run in Stomacher for 3 minutes on high effect. The solution was then transferred to test tubes and 10 ml were inoculated into 10 ml MRS broth. The bacterial concentration was followed during growth at 37° in 5% $CO_2$ in air by quantifying the number of colony forming units (CFU) and the optical density (OD) at 0, 2, 4, 6, 8, 10, 12 and 24 hours. Duplicate samples were taken for the analysis. The results shown in FIG. 11 demonstrate that the capability of growth of the *L. plantarum* 931 cells had been suspended and stored in olive oil on a tissue sheet is just as good as growth of cells from an overnight culture of *L. plantarum* 931. Accordingly, the *L. plantarum* 931 cells were not negatively affected by the storage in olive oil.

Although the present invention has been described in connection with preferred embodiments thereof, it will be appreciated that many modifications and variations of the present invention, including additions, deletions, and substitutions, are possible in light of the above teachings and within the purview of the appended claims without departing from the spirit and intended scope of the invention.

What is claimed is:

1. A hygiene tissue for cleaning of the skin or the urogenital area and transfer of lactic acid producing bacteria to the skin or the urogenital area, comprising:
   at least one first part supplied with at least a cleaning liquid, and
   at least one second part supplied with a composition including a preparation of one or more lactic acid producing bacterial strains includes at least *Lactobacillus plantarum* and a lipid phase comprising at least one lipid, and wherein said preparation of one or more lactic acid producing bacterial strains has a water activity of 0.30 or less,
   wherein the lipid phase is at least one olive oil, canola oil, coconut oil, palm kernel oil, peanut oil, soy bean oil, dimethicone, paraffin oil, or petrolatum,
   wherein the at least one first part and the at least one second part are separate in at least two different parts of the hygiene tissue, and
   wherein the first and second parts are separated by a barrier.

2. The hygiene tissue of claim 1, wherein the water activity is 0.25 or less.

3. The hygiene tissue of claim 1, wherein the water activity is 0.20 or less.

4. The hygiene tissue of claim 1, wherein the preparation of one or more lactic acid producing bacterial strains includes at least *Lactobacillus plantarum* 931 (Deposition No. (DSMZ): 41918 ).

5. The hygiene tissue of claim 1, wherein the hygiene tissue contains $10^4$-$10^{11}$ colony forming units (CFU) of probiotic bacterial cells.

6. The hygiene tissue of claim 5, wherein the amount of probiotic bacterial cells is $10^6$-$10^{11}$ CFU.

7. The hygiene tissue of claim 1, wherein the at least one second part further comprises one or more additional components selected from the group consisting of a caring agent, a water absorbent agent, a pH buffering agent, a perfume, an antioxidant, hydrocortisone or other anti-inflammatory steroid, an antifreezing agent, and a nutrient.

8. The hygiene tissue of claim 7, wherein the water absorbent agent is an inorganic salt.

9. The hygiene tissue of claim 8, wherein the inorganic salt is calcium chloride.

10. The hygiene tissue of claim 7, wherein the pH buffering agent is a weak organic or inorganic acid.

11. The hygiene tissue of claim 10, wherein the weak organic or inorganic acid is lactic acid, ascorbic acid, citric acid, or boric acid.

12. The hygiene tissue of claim 7, wherein the antifreezing agent is skim milk, glucose, glutamate, or glycerol.

13. The hygiene tissue of claim 7, wherein the nutrient is an amino acid, a peptide, a nucleic acid derivative, a vitamin, a salt, a fatty acid, glucose, fructose, ribose, maltose, or lactose.

14. The hygiene tissue of claim 1, wherein the at least one first part further comprises one or more optional cleaning additives selected from the group consisting of an emollient, an emulsifier, a tenside, a moisturizer, a pH-regulating agent, a chelating agent, a viscosity modifier, an antimicrobial agent, a preservative, and a fragrance.

15. The hygiene tissue according to 14, wherein the tenside is a non-ionic surfactant, an amphoteric surfactant, or an anionic surfactant.

16. The hygiene tissue of claim 1, wherein the first and second parts are arranged on different sides of the hygiene tissue.

17. A hygiene tissue for cleaning of the skin or the urogenital area and transfer of lactic acid producing bacteria to the skin or the urogenital area, comprising:
- at least one first part supplied with at least a cleaning liquid, and
- at least one second part supplied with a composition including a preparation of one or more lactic acid producing bacterial strains includes at least *Lactobacillus plantarum* and a lipid phase comprising at least one lipid, and wherein said preparation of one or more lactic acid producing bacterial strains has a water activity of 0.30 or less,
- wherein the lipid phase is at least one olive oil, canola oil, coconut oil, palm kernel oil, peanut oil, soy bean oil, dimethicone, paraffin oil, or petrolatum,
- wherein the at least one first part and the at least one second part are separate in at least two different parts of the hygiene tissue,
- wherein the first and second parts are arranged on different sides of the hygiene tissue, and
- wherein the first part and the second part are separate sheets joined together along two opposite side edges.

18. The hygiene tissue of claim 17, further comprising a barrier including at least one barrier sheet between the first part and the second part and joined thereto along said two opposite side edges.

19. A hygiene tissue for cleaning of the skin or the urogenital area and transfer of lactic acid producing bacteria to the skin or the urogenital area, comprising:
- at least one first part supplied with at least a cleaning liquid, and
- at least one second part supplied with a composition including a preparation of one or more lactic acid producing bacterial strains includes at least *Lactobacillus plantarum* and a lipid phase comprising at least one lipid, and wherein said preparation of one or more lactic acid producing bacterial strains has a water activity of 0.30 or less,
- wherein the lipid phase is at least one olive oil, canola oil, coconut oil, palm kernel oil, peanut oil, soy bean oil, dimethicone, paraffin oil, or petrolatum,
- wherein the at least one first part and the at least one second part are separate in at least two different parts of the hygiene tissue, and
- wherein the second part comprises a first sheet and a second sheet joined together along two opposite side edges and the first part comprises a sheet joined to one of said opposite side edges of the second part and extending along said side edge with one of a side edge of the sheet of the first part.

20. The hygiene tissue of claim 19, wherein the first part comprises a barrier layer separating said second part from said first part when said first part is folded over said second part.

21. The hygiene tissue of claim 19, wherein at least one protective sheet is dispersed between said first sheet and said second sheet of the second part.

22. The hygiene tissue of claim 20, wherein the barrier forms part of a package by being folded around said hygiene tissue, said barrier being large enough to cover the hygiene tissue and being sealed to itself without affecting said first and second parts.

23. The hygiene tissue of claim 17, wherein the water activity is 0.25 or less.

24. The hygiene tissue of claim 17, wherein the hygiene tissue contains $10^6$-$10^{11}$ colony forming units (CFU) of probiotic bacterial cells.

25. The hygiene tissue of claim 17, wherein the at least one second part further comprises one or more additional components selected from the group consisting of a caring agent, a water absorbent agent, a pH buffering agent, a perfume, an antioxidant, hydrocortisone or other anti-inflammatory steroid, an antifreezing agent, and a nutrient.

26. The hygiene tissue of claim 25, wherein the water absorbent agent is an inorganic salt.

27. The hygiene tissue of claim 26, wherein the inorganic salt is calcium chloride.

28. The hygiene tissue of claim 25, wherein the pH buffering agent is a weak organic or inorganic acid.

29. The hygiene tissue of claim 28, wherein the weak organic or inorganic acid is lactic acid, ascorbic acid, citric acid, or boric acid.

30. The hygiene tissue of claim 25, wherein the antifreezing agent is skim milk, glucose, glutamate, or glycerol.

31. The hygiene tissue of claim 25, wherein the nutrient is an amino acid, a peptide, a nucleic acid derivative, a vitamin, a salt, a fatty acid, glucose, fructose, ribose, maltose, or lactose.

32. The hygiene tissue of claim 17, wherein the at least one first part further comprises one or more optional cleaning additives selected from the group consisting of an emollient, an emulsifier, a tenside, a moisturizer, a pH-regulating agent, a chelating agent, a viscosity modifier, an antimicrobial agent, a preservative, and a fragrance.

33. The hygiene tissue according to 32, wherein the tenside is a non-ionic surfactant, an amphoteric surfactant, or an anionic surfactant.

34. A hygiene tissue for cleaning of the skin or the urogenital area and transfer of lactic acid producing bacteria to the skin or the urogenital area, comprising:
- at least one first part supplied with at least a cleaning liquid, and
- at least one second part supplied with a composition including a preparation of one or more lactic acid producing bacterial strains includes at least *Lactobacillus plantarum* and a lipid phase comprising at least one lipid, and wherein said preparation of one or more lactic acid producing bacterial strains has a water activity of 0.30 or less,
- wherein the lipid phase is at least one olive oil, canola oil, coconut oil, palm kernel oil, peanut oil, soy bean oil, dimethicone, paraffin oil, or petrolatum, and
- wherein the at least one first part and the at least one second part are separate in at least two different parts of the hygiene tissues,
- wherein the hygiene tissue is adapted to transfer living one or more lactic acid producing bacterial strains to a user.

35. The hygiene tissue of claim 1, wherein the hygiene tissue is adapted to transfer living one or more lactic acid producing bacterial strains to a user.

36. The hygiene tissue of claim 17, wherein the hygiene tissue is adapted to transfer living one or more lactic acid producing bacterial strains to a user.

37. The hygiene tissue of claim 19, wherein the hygiene tissue is adapted to transfer living one or more lactic acid producing bacterial strains to a user.

* * * * *